United States Patent
Itkowitz et al.

(10) Patent No.: US 11,317,979 B2
(45) Date of Patent: May 3, 2022

(54) SYSTEMS AND METHODS FOR OFFSCREEN INDICATION OF INSTRUMENTS IN A TELEOPERATIONAL MEDICAL SYSTEM

(71) Applicant: INTUITIVE SURGICAL OPERATIONS, INC., Sunnyvale, CA (US)

(72) Inventors: Brandon D. Itkowitz, Sunnyvale, CA (US); Brian D. Hoffman, Mountain View, CA (US); Paul W. Mohr, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 655 days.

(21) Appl. No.: 15/262,867

(22) PCT Filed: Mar. 17, 2015

(86) PCT No.: PCT/US2015/021109
§ 371 (c)(1),
(2) Date: Sep. 12, 2016

(87) PCT Pub. No.: WO2015/142956
PCT Pub. Date: Sep. 24, 2015

(65) Prior Publication Data
US 2017/0165013 A1    Jun. 15, 2017

Related U.S. Application Data

(60) Provisional application No. 61/954,442, filed on Mar. 17, 2014.

(51) Int. Cl.
*A61B 34/35*    (2016.01)
*A61B 34/37*    (2016.01)
(Continued)

(52) U.S. Cl.
CPC .............. *A61B 34/35* (2016.02); *A61B 34/37* (2016.02); *A61B 90/37* (2016.02);
(Continued)

(58) Field of Classification Search
CPC ......... A61B 34/35; A61B 90/37; A61B 34/37; A61B 2090/0811; A61B 2090/371; A61B 2017/00119
See application file for complete search history.

(56) References Cited

U.S. PATENT DOCUMENTS 4,150,326 A * 4/1979 Engelberger ....... G05B 19/4062
                                                    318/563
6,837,883 B2 * 1/2005 Moll ...................... A61B 34/30
                                                    606/1
(Continued)

FOREIGN PATENT DOCUMENTS

CN    1638021 A    7/2005
JP    2004513684 A    5/2004
(Continued)

OTHER PUBLICATIONS

"International Preliminary Report on Patentability for Application No. PCT/US15/21109, dated Sep. 29, 2016, 7 pages".
(Continued)

*Primary Examiner* — Amanda Lauritzen Moher
*Assistant Examiner* — Amy J Shafqat
(74) *Attorney, Agent, or Firm* — Haynes and Boone, LLP

(57) ABSTRACT

A medical imaging system comprises a teleoperational assembly configured to control the movement of a medical instrument including an instrument tip and a processing unit including one or more processors. The processing unit is configured to determine an instrument tip position and determine a position error associated with the instrument tip position. The processing unit is also configured to determine
(Continued)

at least one instrument tip bounding volume based upon the position error and determine if the instrument tip is within a field of view of an imaging instrument.

30 Claims, 21 Drawing Sheets

(51) Int. Cl.
*A61B 90/00* (2016.01)
*A61B 17/00* (2006.01)

(52) U.S. Cl.
CPC ........... *A61B 2017/00119* (2013.01); *A61B 2090/0811* (2016.02); *A61B 2090/371* (2016.02)

(56) References Cited

U.S. PATENT DOCUMENTS

| | | | |
|---|---|---|---|
| 8,086,026 B2* | 12/2011 | Schulz | G06T 7/73 382/154 |
| 2004/0167667 A1* | 8/2004 | Goncalves | G01C 21/12 700/245 |
| 2005/0137751 A1 | 6/2005 | Cox et al. | |
| 2007/0156121 A1* | 7/2007 | Millman | A61M 1/0035 606/1 |
| 2007/0197896 A1* | 8/2007 | Moll | A61B 1/00039 600/407 |
| 2007/0265502 A1* | 11/2007 | Minosawa | A61B 17/3421 600/173 |
| 2007/0293734 A1 | 12/2007 | Coste-Maniere et al. | |
| 2008/0004603 A1* | 1/2008 | Larkin | A61B 1/04 606/1 |
| 2008/0033240 A1* | 2/2008 | Hoffman | A61B 34/70 600/109 |
| 2009/0008873 A1 | 1/2009 | Keilhau | |
| 2009/0036902 A1* | 2/2009 | DiMaio | A61B 34/37 606/130 |
| 2009/0088634 A1* | 4/2009 | Zhao | B25J 9/1689 600/427 |
| 2009/0088773 A1 | 4/2009 | Zhao et al. | |
| 2009/0192523 A1 | 7/2009 | Larkin et al. | |
| 2009/0192524 A1 | 7/2009 | Itkowitz et al. | |
| 2009/0326318 A1* | 12/2009 | Tognaccini | A61B 34/37 600/104 |
| 2010/0039380 A1 | 2/2010 | Lanier | |
| 2010/0228249 A1* | 9/2010 | Mohr | A61B 18/1206 606/41 |
| 2011/0202068 A1* | 8/2011 | Diolaiti | A61B 34/74 606/130 |
| 2011/0230896 A1* | 9/2011 | Wallace | A61B 5/042 606/130 |
| 2012/0209272 A1* | 8/2012 | Ranawat | A61B 17/1626 606/80 |
| 2013/0060278 A1* | 3/2013 | Bozung | A61B 17/00234 606/205 |
| 2013/0345718 A1* | 12/2013 | Crawford | A61B 17/025 606/130 |
| 2014/0055489 A1 | 2/2014 | Itkowitz et al. | |
| 2017/0172662 A1* | 6/2017 | Panescu | A61B 34/37 |

FOREIGN PATENT DOCUMENTS

| | | |
|---|---|---|
| JP | 2005143918 A | 6/2005 |
| JP | 2012521885 A | 9/2012 |
| WO | WO-2007114975 A2 | 10/2007 |
| WO | WO-2008002830 A2 | 1/2008 |
| WO | WO-2010117685 A2 | 10/2010 |

OTHER PUBLICATIONS

Extended European Search Report for Application No. EP15765724.8, dated Oct. 27, 2017, 6 pages.
International Search Report and Written Opinion for Application No. PCT/US15/21109, dated Jun. 8, 2015, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP19181 852.5, dated Oct. 11, 2019, 6 pages.

* cited by examiner

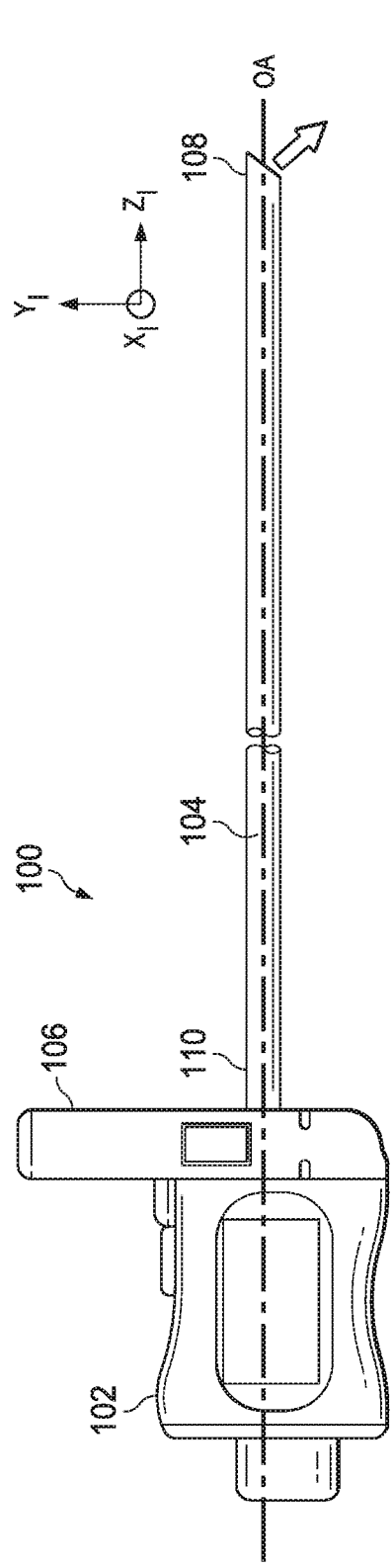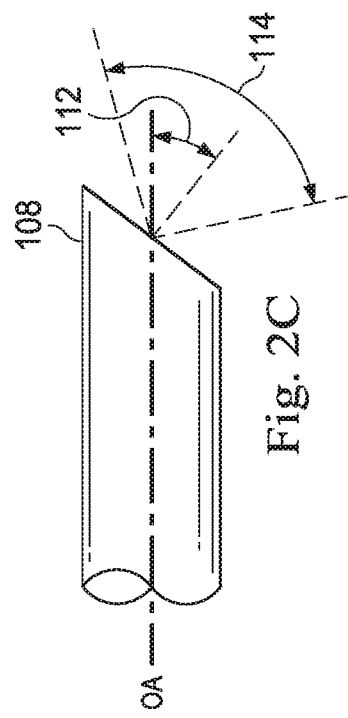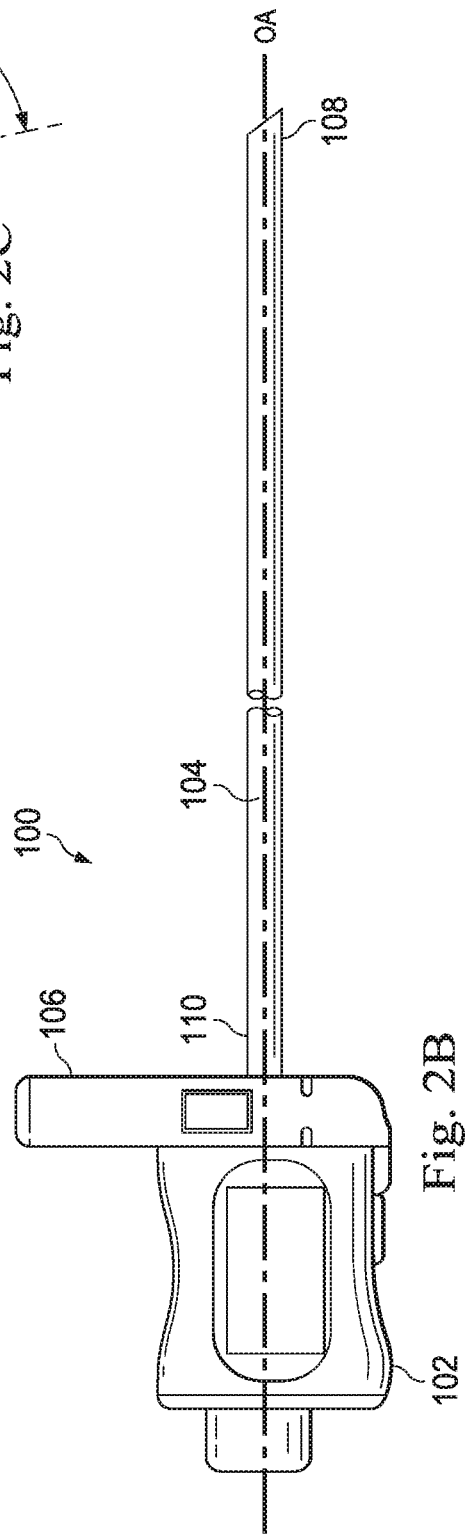

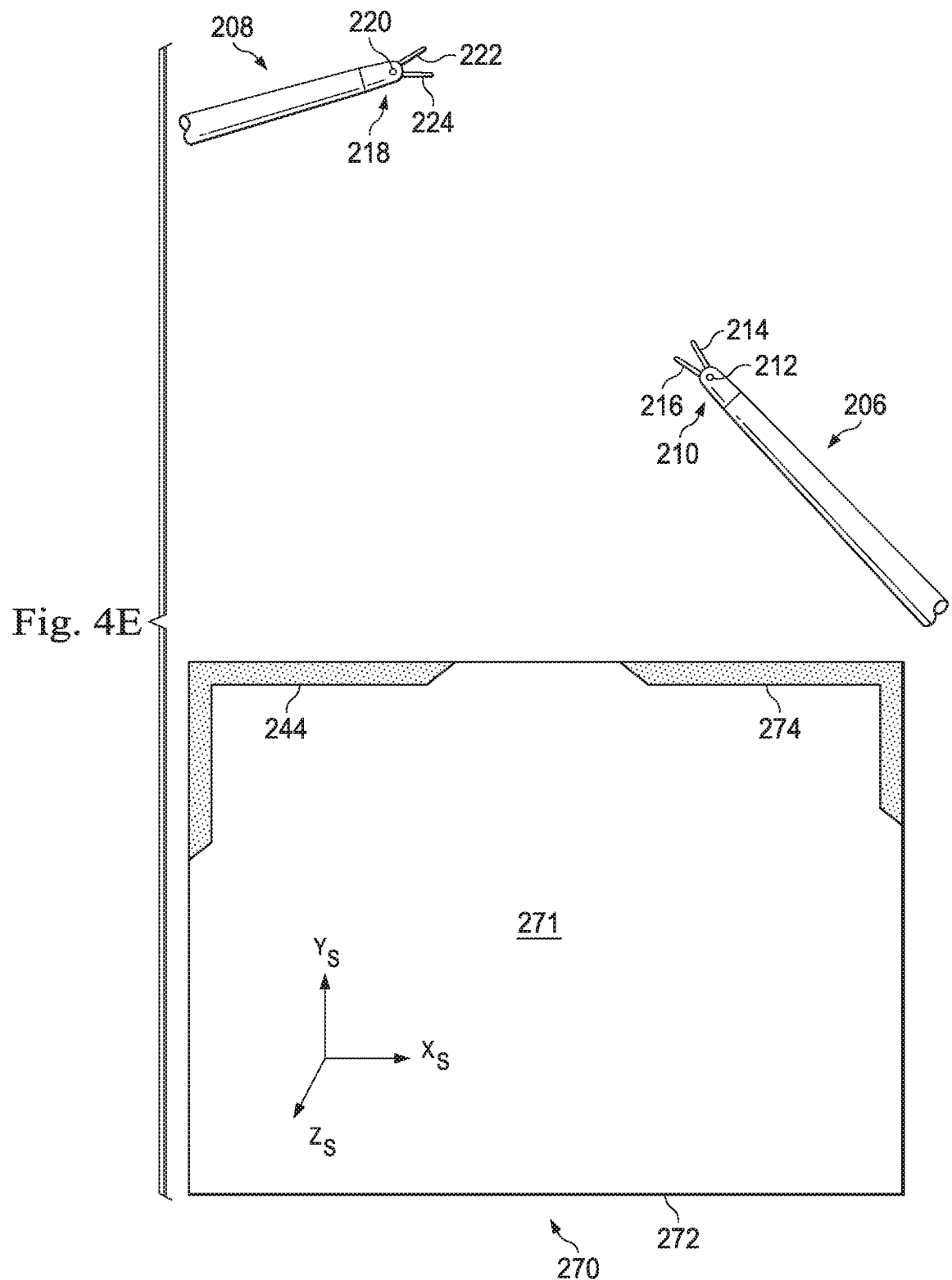

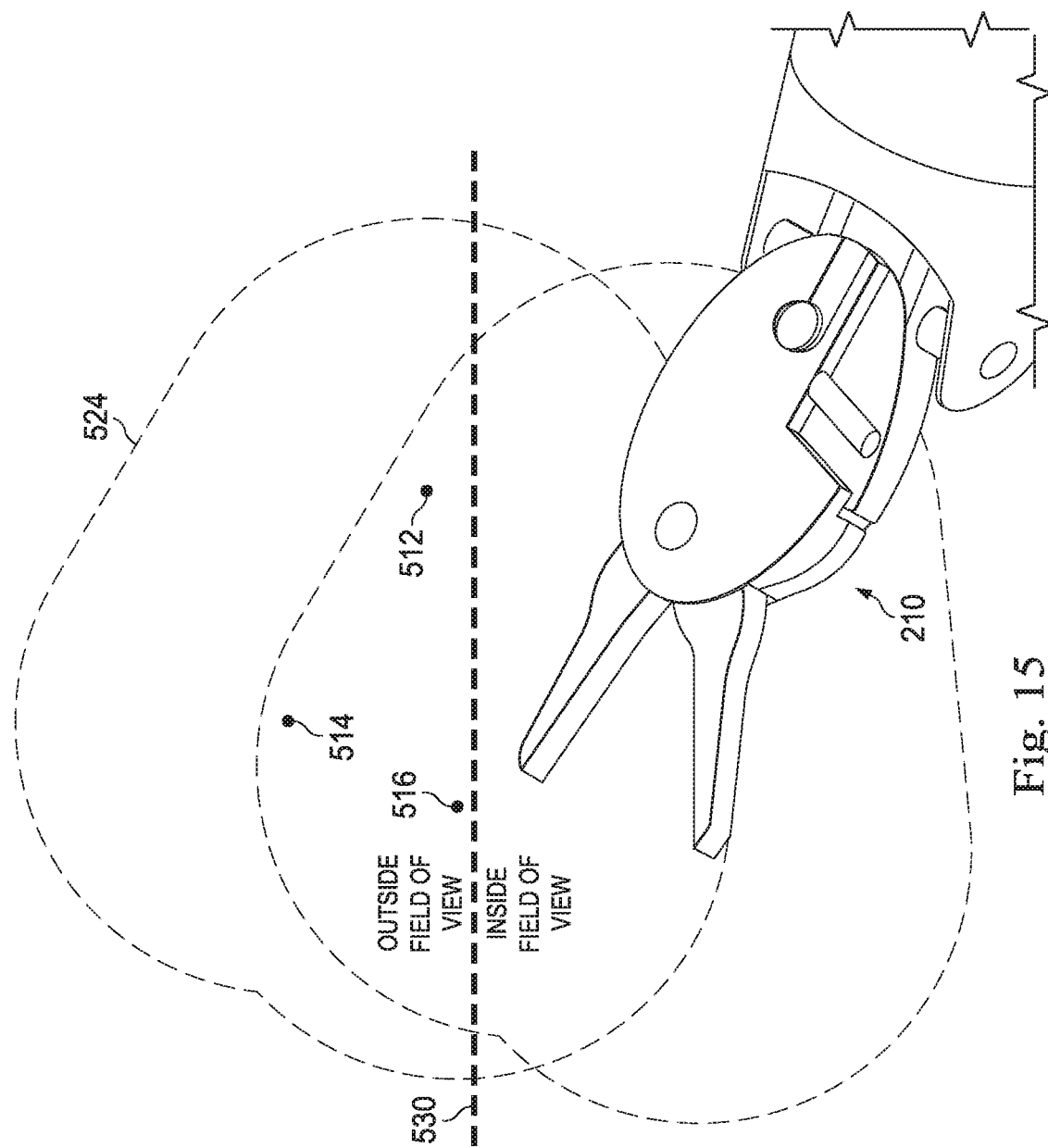

SYSTEMS AND METHODS FOR OFFSCREEN INDICATION OF INSTRUMENTS IN A TELEOPERATIONAL MEDICAL SYSTEM

PRIORITY

This patent application is the U.S. national phase of International Application No. PCT/US2015/021109, filed Mar. 17, 2015, which designated the U.S. and claims priority to and the benefit of the filing date of U.S. Provisional Patent Application 61/954,442, titled "Systems and Methods for Offscreen Indication of Instruments in a Teleoperational Medical System," filed Mar. 17, 2014, which is are incorporated herein by reference in its their entirety.

FIELD

The present disclosure is directed to systems and methods for performing a teleoperational medical procedure and more particularly to systems and methods for providing an indication of the location of a teleoperational instruments located outside of an endoscope's field of view.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. In a teleoperational medical system, instruments may be controlled without being visible to a user in the field of view provided by the imaging instrument. Inadvertent movement of the instrument outside of the field of view, creates a safety risk. Additionally, clinicians may lose track of instruments that are located outside of the field of view. Systems and methods are needed to provide a clinician with an indication of the location of instruments outside of the field of view, while minimizing the occurrence of false indications.

SUMMARY

The embodiments of the invention are summarized by the claims that follow below.

In one embodiment, a medical imaging system comprises a teleoperational assembly configured to control the movement of a medical instrument including an instrument tip and a processing unit including one or more processors. The processing unit is configured to determine an instrument tip position and determine a position error associated with the instrument tip position. The processing unit is also configured to determine at least one instrument tip bounding volume based upon the position error and determine if the instrument tip is within a field of view of an imaging instrument.

In another embodiment, a method of imaging comprises determining an instrument tip position for a medical instrument controlled by a teleoperational assembly and determining a position error associated with the instrument tip position. The method further comprises determining at least one instrument tip bounding volume based upon the position error and determining if the instrument tip is within a field of view of an imaging instrument.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 2A illustrates an off-axis endoscopic imaging instrument in first orientation.

FIG. 2B illustrates the off-axis endoscopic imaging instrument of FIG. 2A in a second orientation.

FIG. 2C illustrates the distal end of the off-axis endoscopic imaging instrument of FIG. 2A.

FIG. 4E illustrates another field of view of the surgical workspace of FIG. 4A, with both of the instruments outside of the field of view.

FIGS. 12-15 illustrate the influence of instrument tip distance from the imaging instrument in determining whether the instrument tip is outside of the imaging instrument field of view.

DETAILED DESCRIPTION

Figure 1A:
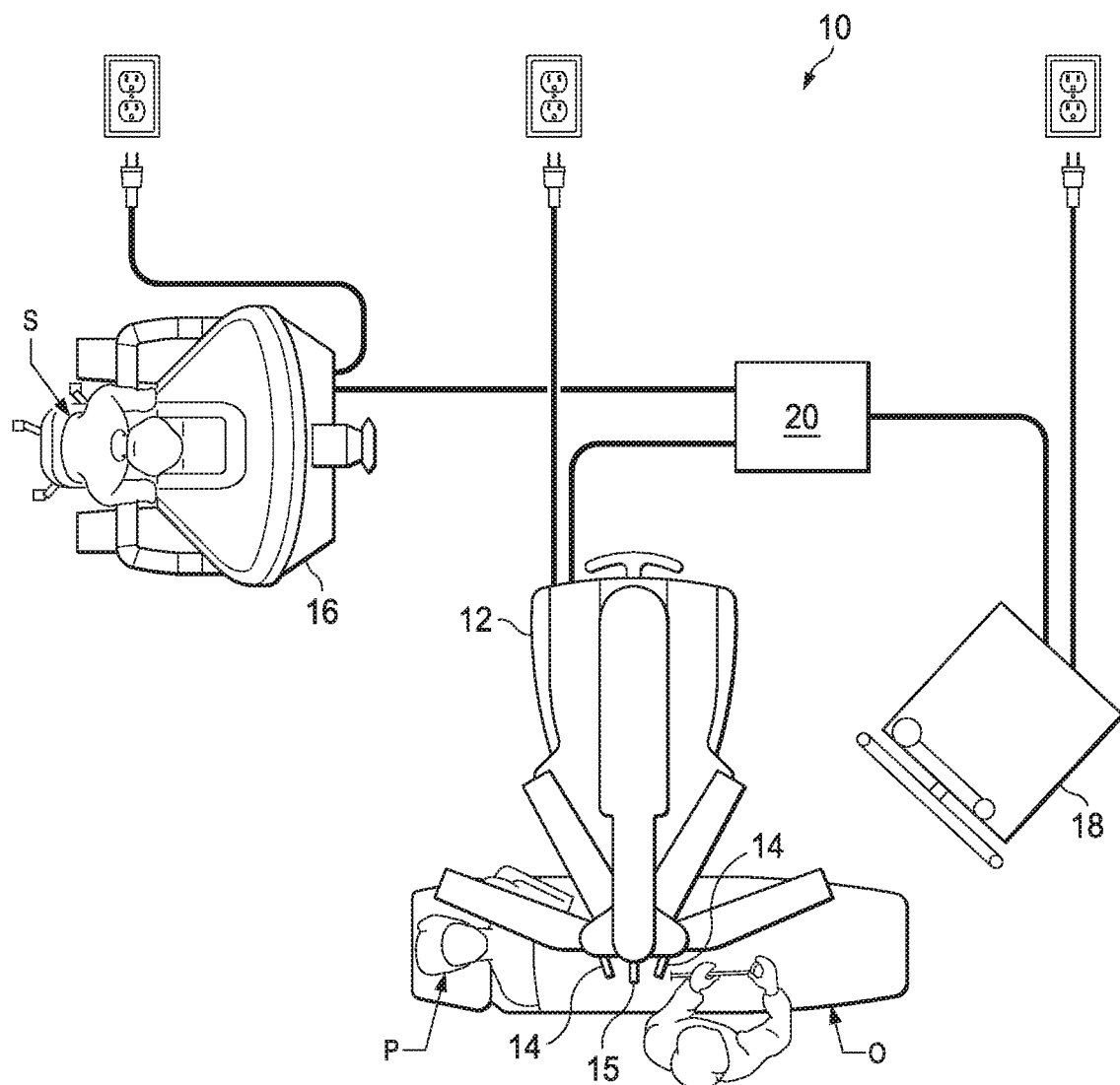
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperational assembly 12 to orient the endoscope 15. An electronics cart 18 can be used to process the images of the surgical site for subsequent display to the surgeon S through the surgeon's console 16. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 10 also includes a control system 20. The control system 20 includes at least one memory and at least one processor (not shown), and typically a plurality of processors, for effecting control between the medical instrument system 14, the operator input system 16, and an electronics system 18. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth®, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The teleoperational medical system 10 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
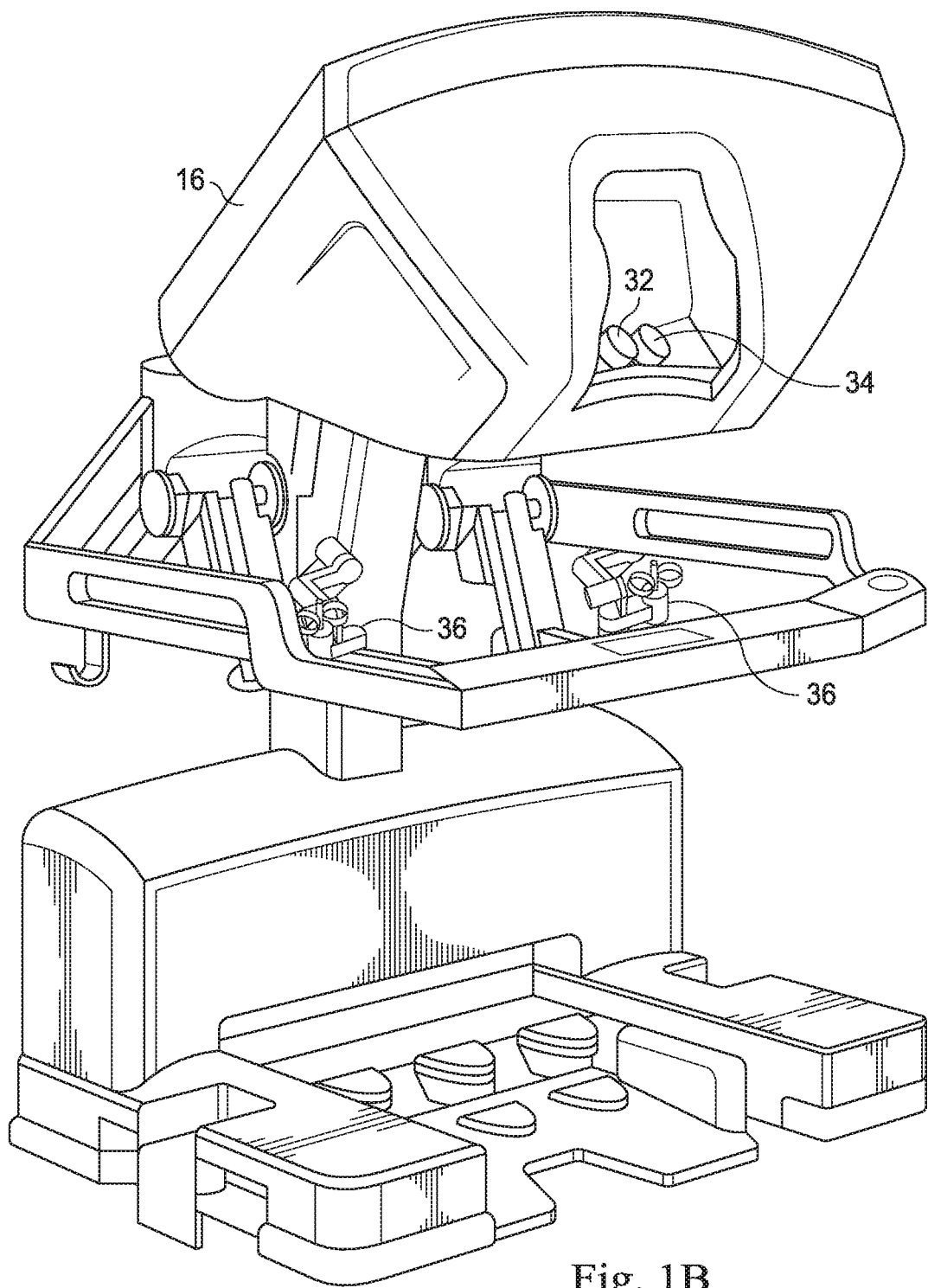
FIG. 1B is a perspective view of a surgeon's control console for a teleoperational medical system, in accordance with many embodiments.

FIG. 1B is a perspective view of the surgeon's console 16. The surgeon's console 16 includes a left eye display 32 and a right eye display 34 for presenting the surgeon S with a coordinated stereo view of the surgical site that enables depth perception. The console 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36.

Figure 1C:
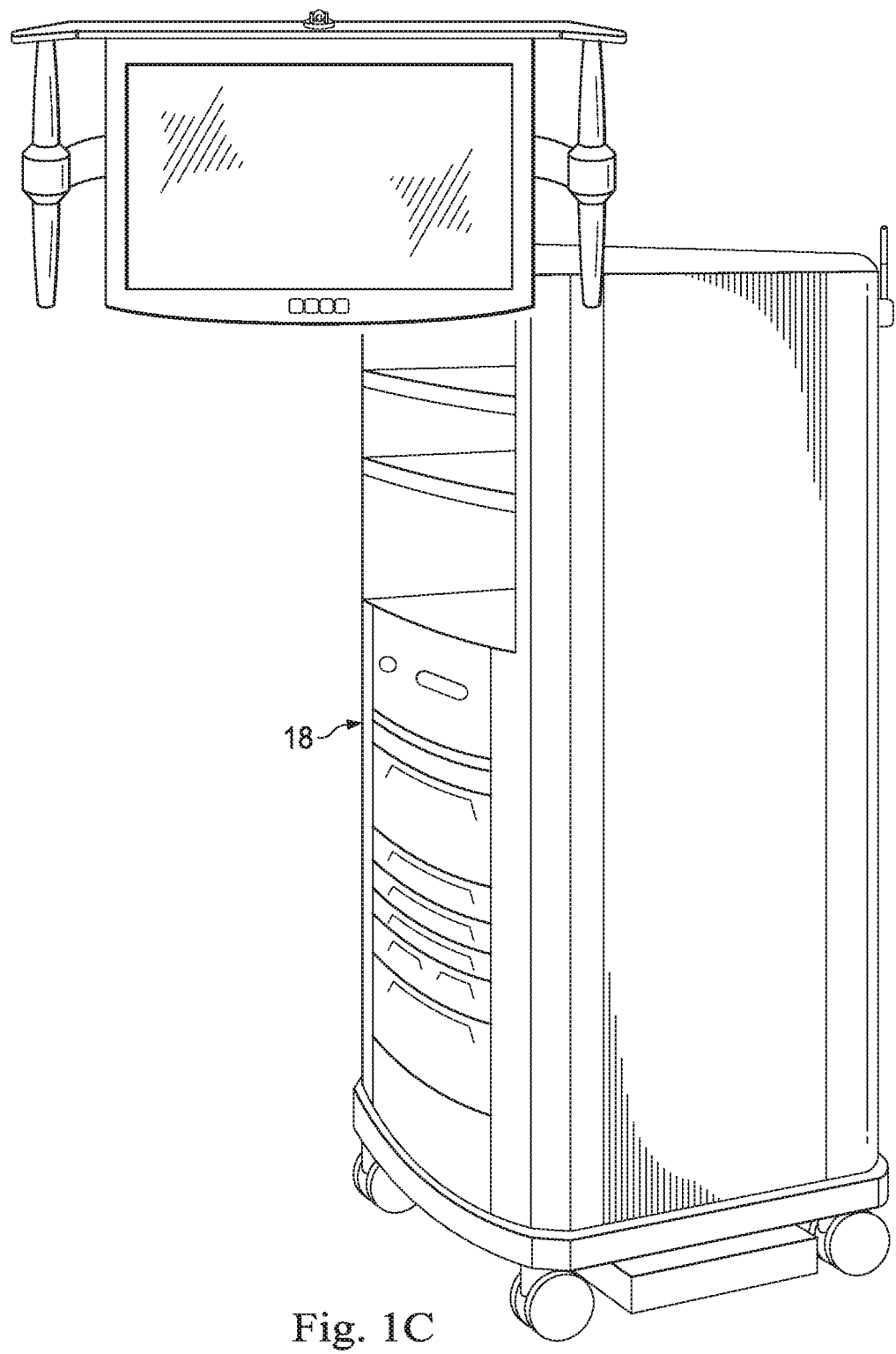
FIG. 1C is a perspective view of a teleoperational medical system electronics cart, in accordance with many embodiments.

FIG. 1C is a perspective view of the electronics cart 18. The electronics cart 18 can be coupled with the endoscope 15 and can include a processor to process captured images for subsequent display, such as to a surgeon on the surgeon's console, or on another suitable display located locally and/or remotely. For example, where a stereoscopic endoscope is used, the electronics cart 18 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. The electronics cart 18 may also include a display monitor and components of the control system 20.

Figure 1D:
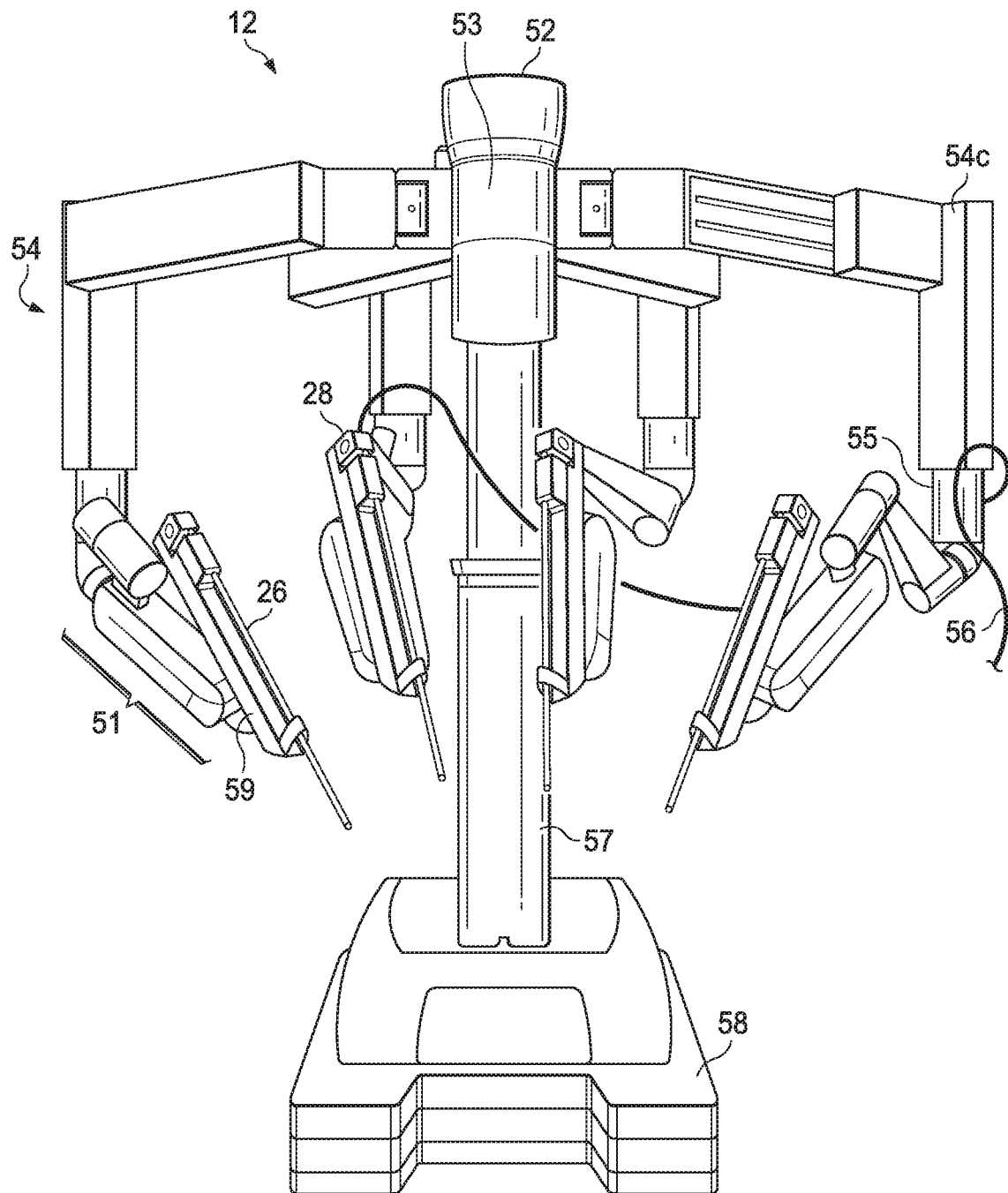
FIG. 1D is a perspective view of a patient side cart, according to one example of principles described herein.

FIG. 1D is a perspective view of one embodiment of a teleoperational assembly 12 which may be referred to as a patient side cart. The patient side cart 12 shown provides for the manipulation of three surgical tools 26 (e.g., instrument systems 14) and an imaging device 28 (e.g., endoscopic imaging system 15), such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

The patient side cart 22 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 22 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument 26 via a manipulator spar 59. The manipulator arms 51 may be teleoperatable. In some examples, the arms 54 connecting to the orienting platform are not teleoperatable. Rather, such arms 54 are positioned as desired before the surgeon 18 begins operation with the teleoperative components.

Endoscopic imaging systems (e.g., systems 15, 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Endoscopes may be provided with different viewing angles including a 0° viewing angle for forward axial viewing or viewing angles between 0°-90° for forward oblique viewing. Digital image based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. FIG. 2A illustrates a rigid off-axis stereo endoscopic imaging instrument 100 including a handle 102 and a shaft 104 rigidly coupled to the handle. A roll adaptor 106 is coupled rotatably coupled to the shaft 104 and/or the handle 102. The shaft includes a distal end 108 and a proximal end 110 and houses a distal image storage device, lens systems, optical fibers, or other stereo image capture and transmission components (not shown). The shaft 104 extends along an optical axis OA. As shown in FIG. 2C, the instrument 100 has an angle of view 112 and a conical optical field of view 114. In this embodiment, the angle of view is approximately 30° but may be any angle suitable for oblique angle viewing with respect to the optical axis OA. Responsive to manual or teleoperational control, the teleoperational assembly (e.g., assembly 12) may be operated to rotate the imaging instrument 100, including the instrument body 102 and the shaft 104, about the optical axis OA. FIG. 2A illustrates the imaging instrument 100 with a −30° or downward angle with respect to the optical axis OA. FIG. 2B illustrates the imaging instrument 100 rotated 180° with a +30° or upward angle with respect to the optical axis OA. The terms "up", "down", "upward, and "downward" are used for illustrative purposes only to label generally opposite directions and are not intended to be limiting.

Figure 3:
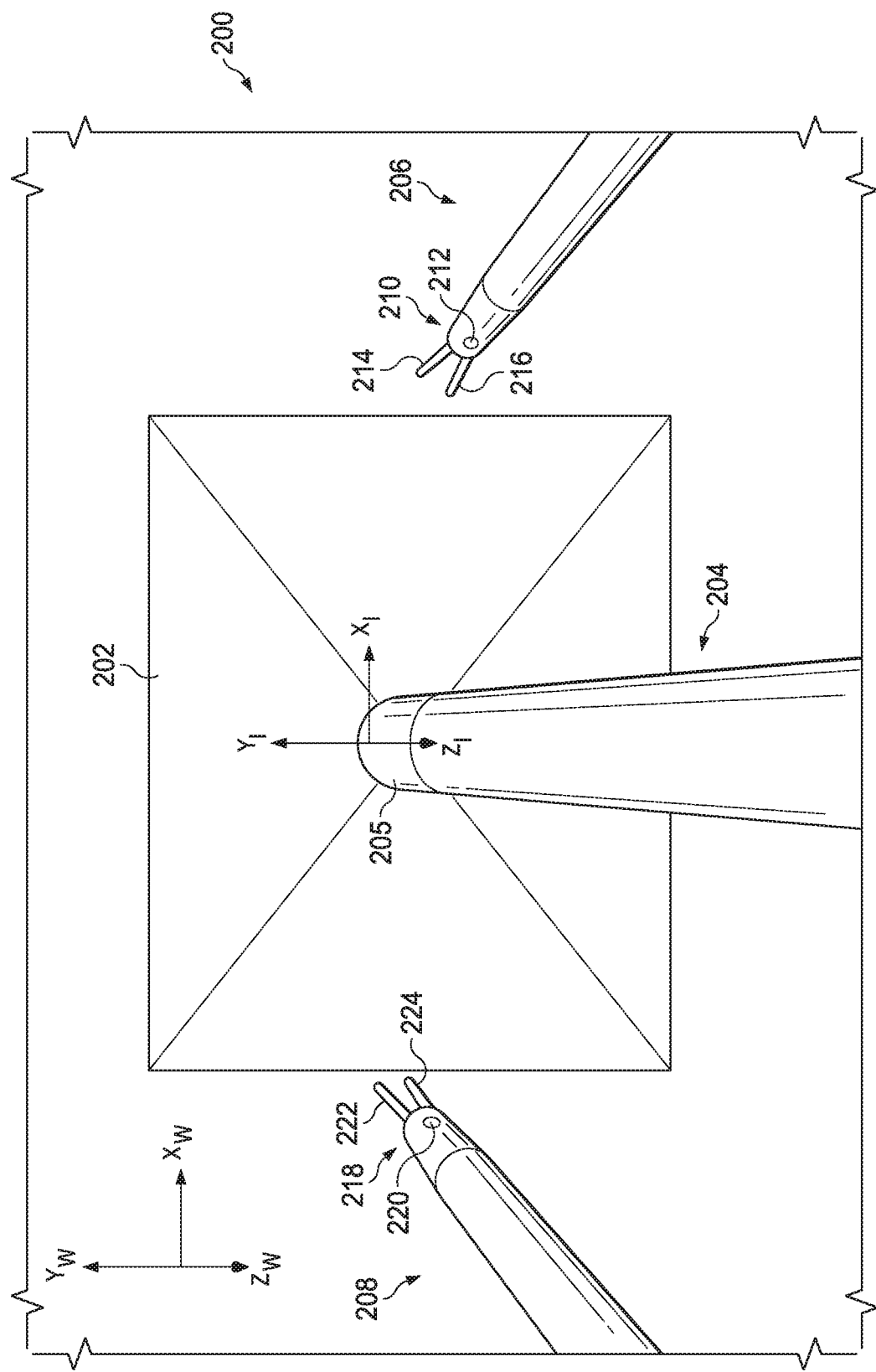
FIG. 3 illustrates a surgical workspace surrounding an imaging instrument field of view.

FIG. 3 illustrates a surgical workspace 200 surrounding an imaging instrument field of view 202 for an imaging instrument 204 (e.g., imaging instruments 15, 100). The imaging instrument 204 has a distal end 205. Two surgical instruments 206, 208 (e.g., instruments 14) are operable within the workspace 200. In this embodiment, field of view 202 has a three-dimensional pyramidal frustum shape. If the imaging instrument 204 is a stereoscopic imaging instrument with two imaging devices, the field of view of the imaging instrument is the combined volume of the three-dimensional pyramidal frustums for each imaging device of the imaging instrument. In alternative embodiments, the three-dimensional field of view for the imaging instrument or imaging devices may be a conical frustum shape. The medical instrument 206 includes a distal instrument tip 210 which in this embodiment is a two-finger actuatable tip including a proximal tip portion 212 a first distal tip portion 214 and a second distal tip portion 216. Similarly, the medical instrument 208 includes a distal instrument tip 218 which in this embodiment is a two-finger actuatable tip including a proximal tip portion 220 a first distal tip portion 222 and a second distal tip portion 224.

In the configuration of FIG. 3, the medical instruments 206, 208 are outside of the field of view of the imaging instrument 204. The determination of whether the instruments 206, 208 are inside or outside of the field of view of the imaging instrument 204 may be based upon the calculated location of the instrument distal tips 210, 218 as is described in further detail at FIG. 7. The surgical workspace of FIG. 3 has a world coordinate system ($X_W$, $Y_W$, $Z_W$) for world space and the distal end of the imaging instrument has an imaging or endoscope coordinate system ($X_I$, $Y_I$, $Z_I$) for endoscope space.

Figure 4A:
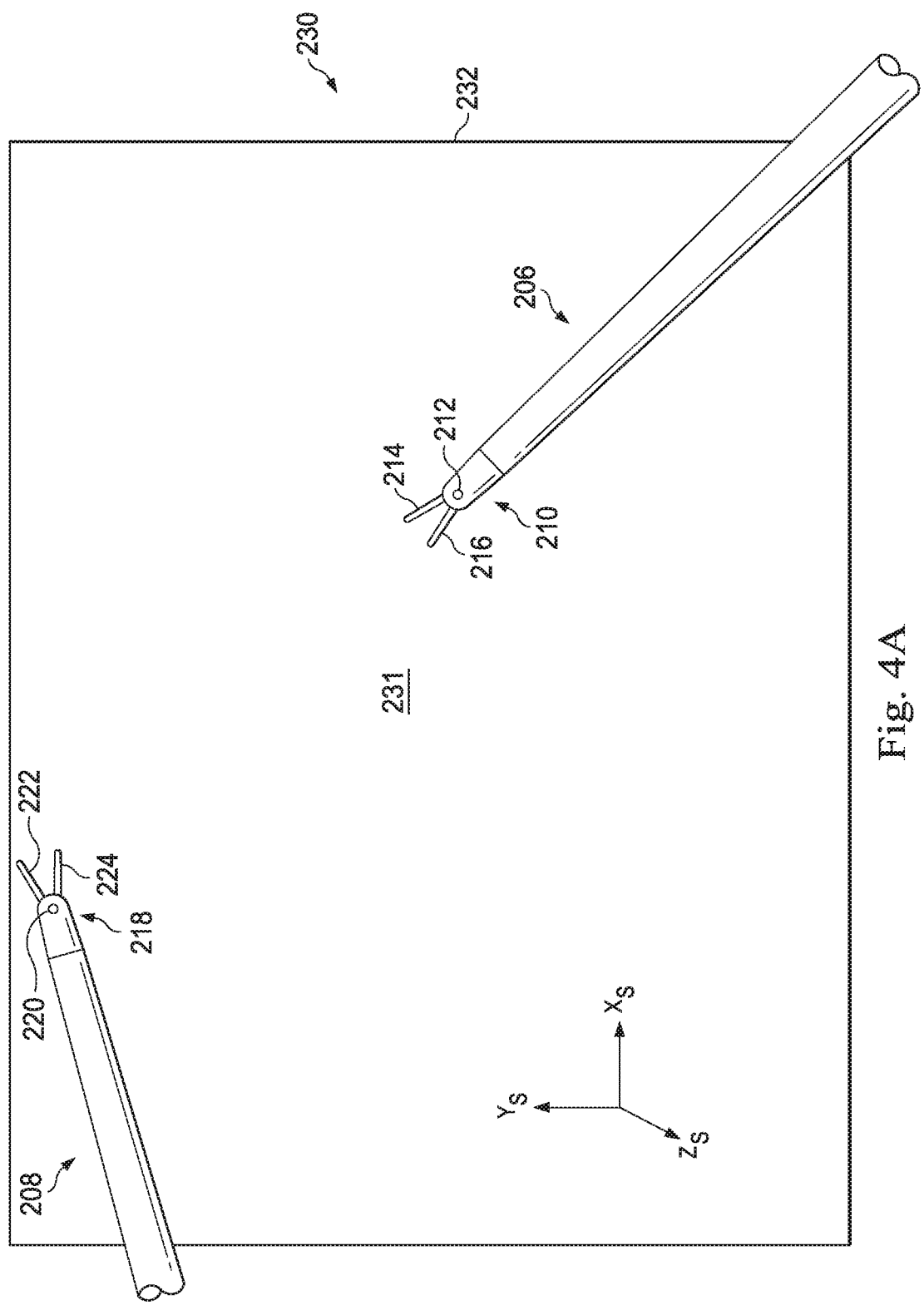
FIG. 4A illustrates a field of view of a surgical workspace with two instruments visible in the field of view.

FIG. 4A illustrates a displayed image 230 of a field of view 231 of the imaging instrument 204 in the surgical workspace 200. The instruments 206, 208 are visible in the displayed image 230. In this configuration, the instruments 206, 208 are considered be "on-screen," that is, on a display screen displaying the image 230. The field of view 231 has a boundary 232. The displayed image has a display or screen coordinate system ($X_S$, $Y_S$, $Z_S$) for display or screen space. In a stereoscopic imaging system, there may be separate screen coordinate systems for each of the left and right screens.

Figure 4B:
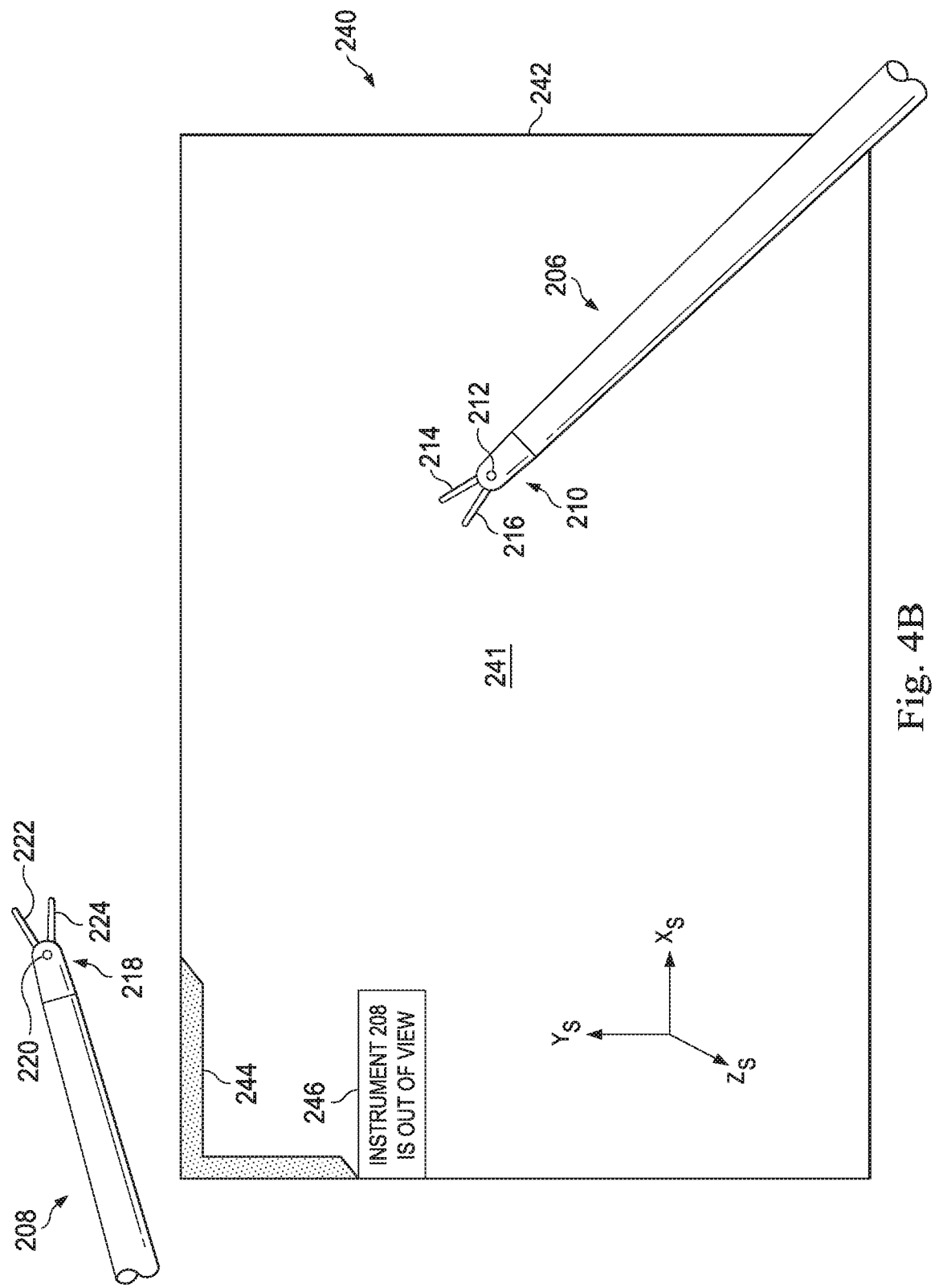
FIG. 4B-4D illustrate other fields of view of the surgical workspace of FIG. 4A, with one of the instruments outside of the field of view.

FIG. 4B illustrates a displayed image 240 of a field of view 241 of the imaging instrument 204 in the surgical workspace 200. The field of view 241 has a boundary 242. The field of view of the instrument 204 may be changed, for example, by zooming-in, zooming-out, moving in a pitch motion, moving in a yaw motion, or rolling between an upward viewing angle and a downward viewing angle. The instrument 206 remains within the field of view 241 and thus is visible in the displayed image 240. The instrument 206 is thus considered to be on-screen. The instrument 208 is not in the field of view 241 and thus is not visible in the displayed image 240. The instrument 208 is thus considered to be offscreen.

Because the instruments 206, 208 may be teleoperationally controlled without being visible to a clinician in the field of view, inadvertent movement of an instrument outside of the field of view, creates a safety risk. Additionally, clinicians may lose track of instruments that are located outside of the field of view. To minimize these risks, out-of-view instrument indicators may be visually or audibly presented to increase the clinician's awareness of the location of instruments not visible within the field of view. For example, as shown in FIG. 4B, an out-of-view instrument indicator 244 is provided along the boundary 242 of the field of view 241 to indicate that instrument 208 is located out of the field of view, in the general direction of the indicator. In this embodiment, the indicator 244 is a graphical bar, but in other embodiments may be a series of dots, or an icon, an alpha-numeric indicator. In addition to or alternative to the visual indicator 244, an audible out-of-view indicator such as a beeping sound or a language-based instruction may alert the clinician that the instrument 208 is out of the field of view. The audible cue may pan between left and right speakers of the surgeon's console to reinforce the instrument position relative to the view. Alternatively, the audible cue may emit from the left or right speaker in correspondence with the left or right hand control associated with the instrument. In addition to or alternative to the visual indicator 244, textual information 246 related to the out-of view instrument may be provided to alert the clinician and/or to provide identifying information about the instrument or an instruction to visualize the instrument.

In various embodiments, the use of an out-of-view indicator may be limited to avoid becoming a distraction to the clinician. The use of the out-of-view indicator may be context-sensitive such that the out-of-view indicator may only be displayed during certain modes of operation of the teleoperational system. For example, the out-of-view indicator may be displayed during a mode of the system in which the operator controls movement of the imaging system, a mode which may be known as a camera control mode.

As another example, the out-of-view indicator may be displayed while the system awaits input from the operator to take control of an associated instrument. As another example, the out-of-view indicator may be displayed for a few seconds after initiating a mode of the system in which the operator controls movement of the instruments, a mode which may be known as a following mode. In still other alternative embodiments, the out-of-view indicator may be disabled or selectively enabled when the clinician wants to learn about the location of out-of-view instruments. In some embodiments, the clinician must provide an acknowledgement that the instrument tip is outside of the field of view before operation of the out of view instrument is enabled. Additional warnings or acknowledgements may be used for energy emitting devices, sharp devices, or devices that provide an increased patient risk if used without visualization. In some embodiments an out-of-view indicator may be provided for instruments that are within the field of view but not visible due to occluding tissue or other structures.

Figure 4C:
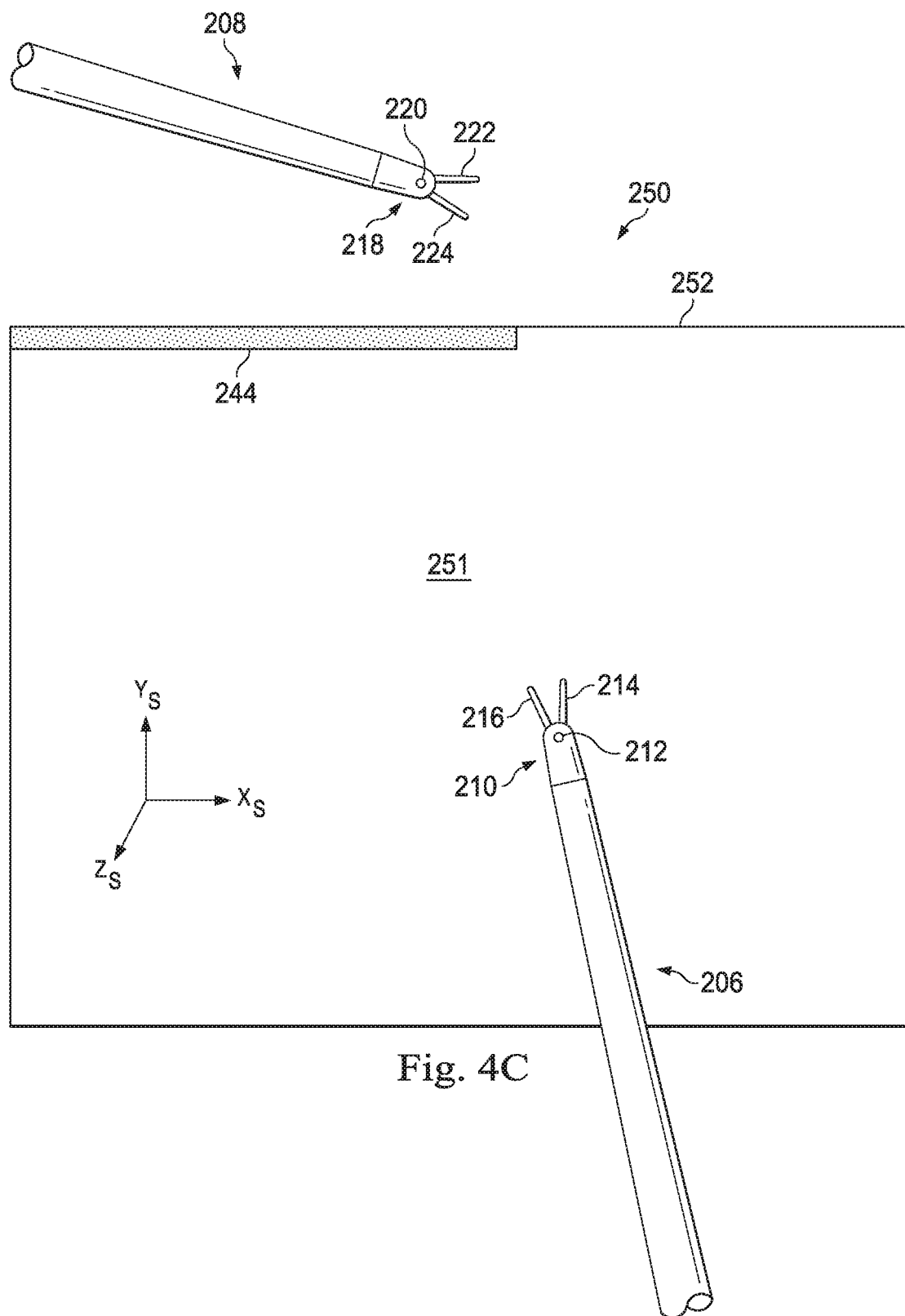

FIG. 4C illustrates a displayed image 250 of a field of view 251 of the imaging instrument 204 in the surgical workspace 200 after moving the imaging instrument 204 from the position or orientation it was in for FIG. 4B. The field of view 251 has a boundary 252. The instrument 206 remains within the field of view 251 and thus is visible in the displayed image 250. The instrument 208 is out of the field of view 251 and thus is not visible in the displayed image 250. The out-of-view indicator 244 has relocated to a different location along the boundary 252 to reflect the location of the out of view instrument after the imaging instrument has moved. In some embodiments, the total length of the indicator 244 may remain the same as the imaging instrument moves. In alternative embodiments, the indicator may scale to indicate a distance of the out of view instrument from the field of view.

Figure 4D:
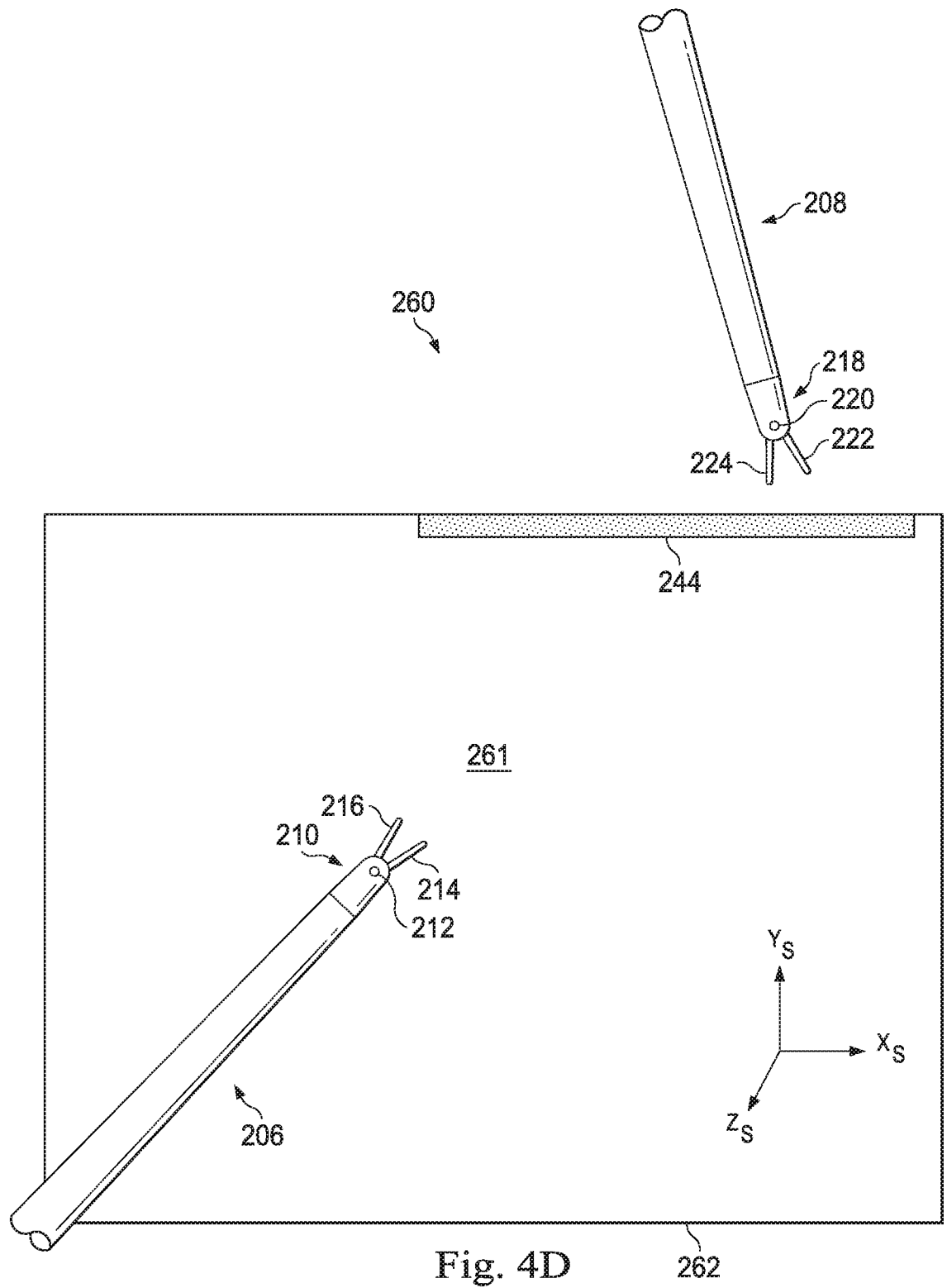

FIG. 4D illustrates a displayed image 260 of a field of view 261 of the imaging instrument 204 in the surgical workspace 200 after moving the imaging instrument 204 from the position or orientation it was in for FIG. 4C. The field of view 261 has a boundary 262. The instrument 206 remains within the field of view 261 and thus is visible in the displayed image 260. The instrument 208 is out of the field of view 261 and thus is not visible in the displayed image 260. The out-of-view indicator 244 has further relocated along the boundary 262 to reflect the location of the out of view instrument after the imaging instrument has moved.

FIG. 4E illustrates a displayed image 270 of a field of view 271 of the imaging instrument 204 in the surgical workspace 200 after rolling the imaging instrument 204 from the viewing angle up configuration it was in for FIG. 4A to a viewing angle down configuration. The field of view 271 has a boundary 272. The instruments 206 and 208 are both out of the field of view 271 and thus are not visible in the displayed image 270. The out-of-view indicator 244 indicates the general direction of the out of view instrument 208 and an out-of-view indicator 274 indicates the general direction of the out of view instrument 210.

Figure 4F:
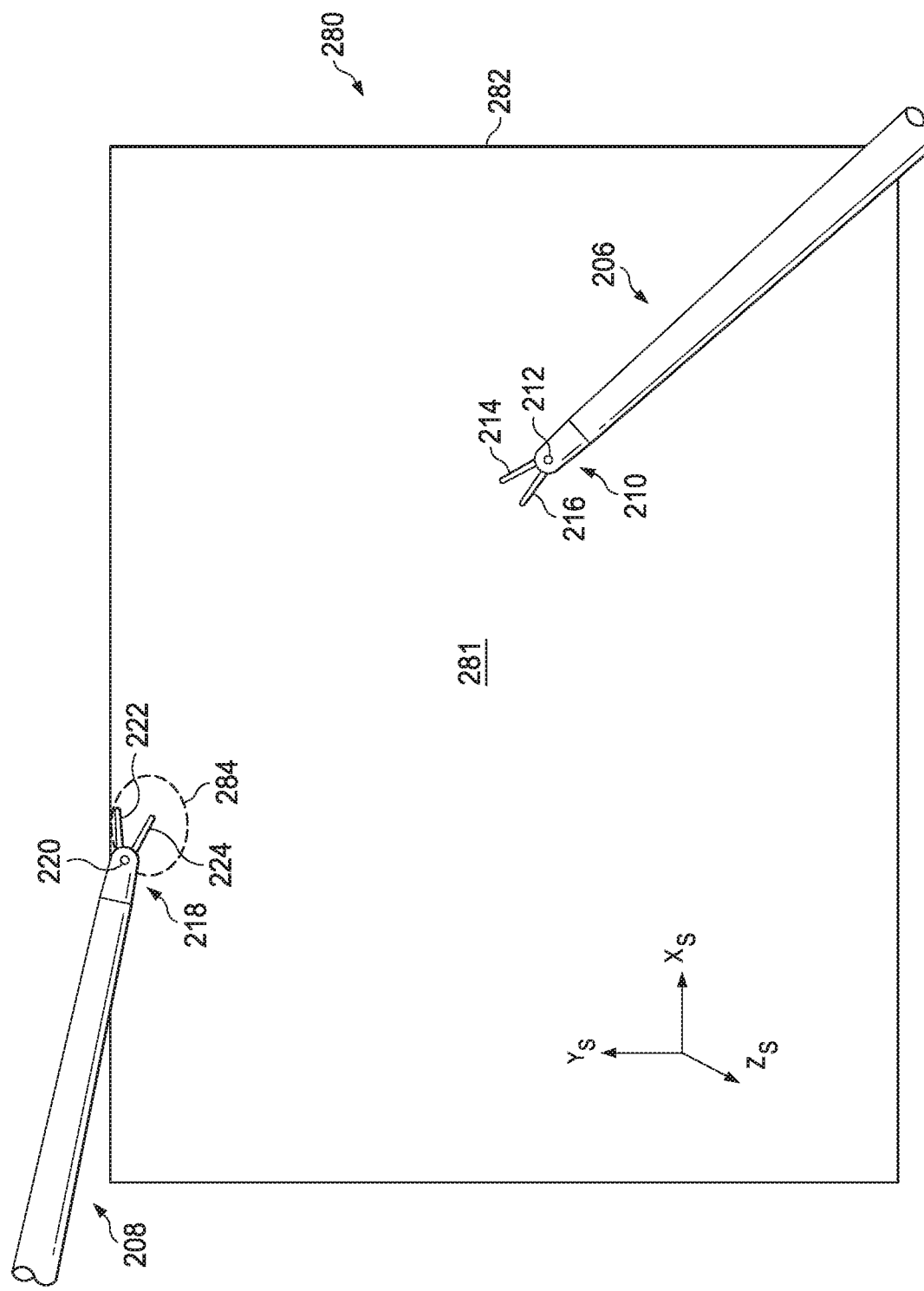
FIG. 4F illustrates another field of view of the surgical workspace of FIG. 4A with one of the instruments located near the boundary of the field of view.

FIG. 4F illustrates a displayed image 280 of a field of view 281 of the imaging instrument 204 in the surgical workspace 200. The field of view 271 has a boundary 282. The instruments 206 and 208 are both within the field of view 281 and thus are visible in the displayed image 280. A warning indicator 284 may be provided to indicate that the instrument tip 218 is nearing the boundary 282. In this embodiment, the warning indicator 284 is a ring, but in alternative embodiments, may be another type of graphical symbol or an auditory indicator. The indicator may change (e.g., flash) as the tip 218 moves nearer to the boundary 282. The warning indicator 284 may appear in the displayed image 280 when any of the instrument tips move within a predefined distance (e.g., 1 cm.) from the boundary 282.

As explained above, the determination of whether the instruments 206, 208 are inside or outside of the field of view of the imaging instrument 204 may be based upon the calculated location of the instrument distal tips 210, 218. Because of small error factors associated with the teleoperational system, the instrument, and/or the imaging system, the determination of the location of the instrument distal tips 210, 218 with respect to the imaging instrument 204 has an associated cumulative error factor. To avoid providing false-positive out-of-view indicators to a clinician, the determination of whether an instrument tip is out of the imaging system field of view may be biased by estimating the range of possible locations for the distal tip and suppressing an out-of-view indicator if any or a designated percentage of the estimated possible locations for the distal tip are within the field of view. The sensitivity of the bias may be adjusted based upon the clinician's tolerance for false-positive out-of-view indicators.

Figure 5:
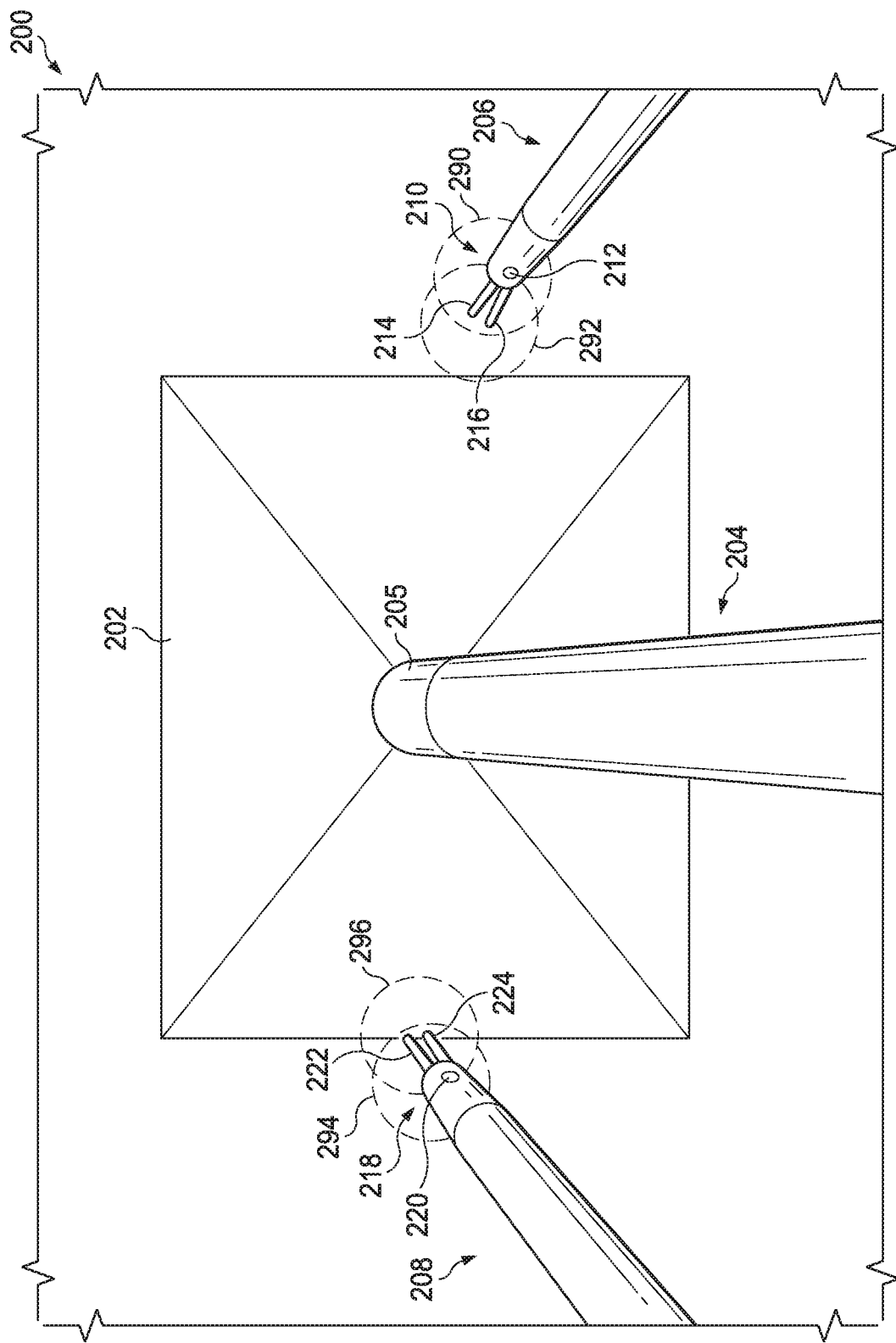
FIG. 5 illustrates a surgical workspace surrounding an imaging instrument field of view and including instruments with error bounding volumes.

FIG. 5 illustrates the surgical workspace 200 surrounding the imaging instrument field of view 202 for the imaging instrument 204. In this illustration, the position errors associated with the instrument tips 210, 218 of medical instruments 206, 208 are shown. A set of error bounding volumes is associated with each instrument tip 210, 218. The error bounding volumes may represent the predicted locations of the distal and proximal ends of the tip portions to within a high degree of certainty such as 90-99%. An error bounding volume 290 represents the predicted locations of the proximal tip portion 212 of the instrument tip 210. An error bounding volume 292 represents the predicted locations of the distal tip portions 214, 216 of the instrument tip 210. In this configuration, the distal tip portions 214, 216 are arranged in a grip-closed configuration (e.g., an angle between the tip portions is approximately zero) in which the distal tip portions are close together. Thus, a single bounding volume 292 may be used to approximate the distal tip portions 214, 216. If the distal tip portions 214, 216 are arranged in a grip-open configuration (e.g., an angle between the tip portions is substantially larger than zero), a separate bounding volume may be used to approximate the location of each distal tip portion. An error bounding volume 294 represents the predicted locations of the proximal tip portion 220 of the instrument tip 218. An error bounding volume 296 represents the predicted locations of the distal tip portions 222, 224 of the instrument tip 218. The bounding volumes may be used as the basis for determining whether to present an out-of-view indicator to a clinician. For example, both boundary volumes 290, 292 are outside of the field of view 202, and thus an out-of-view indicator would be generated for instrument 206. At least one of the bounding volumes 294, 296 is within the field of view 202 and thus an out-of view indicator would not be generated for instrument 208. In alternative embodiments, a bounding volume may also be provided for the field of view in recognition of error associated with the boundaries of the field of view. Similarly, if the bounding volumes of the field of view intersect the bounding volumes of an instrument, an out-of-view indicator will not be presented to a clinician.

Figure 6:
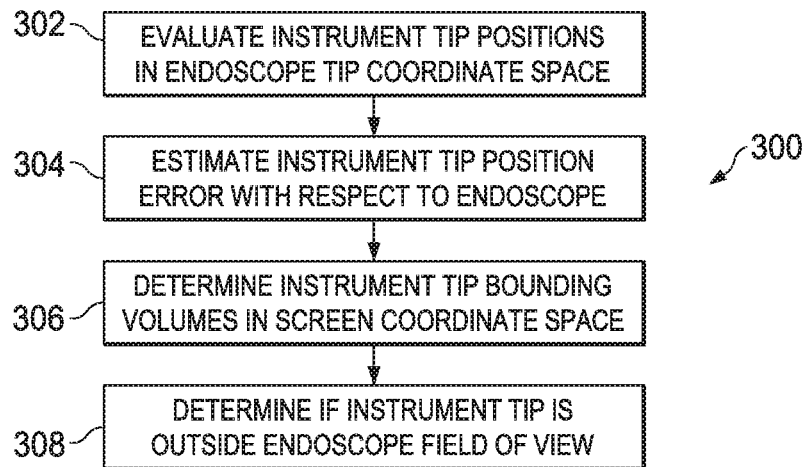
FIG. 6 is a method for determining whether an instrument is outside of a field of view.

FIG. 6 illustrates a method 300 for determining whether an instrument is outside of a field of view. At process 302, the method 300 includes evaluating instrument tip positions in the endoscope tip coordinate space as described in further detail in FIG. 7. At process 304, the method 300 includes estimating instrument tip position error with respect to the distal tip of the endoscope as described in further detail in FIG. 8. At process 306, the method 300 includes determining the instrument tip bounding volumes in screen coordinate space as described in further detail in FIG. 9. At process 308, the method 300 includes determining if the instrument tip is outside of the endoscope field of view as described in further detail in FIG. 10. Although an imaging instrument is referred to as an endoscope in FIGS. 6-10, other imaging instruments may be used.

Figure 7:
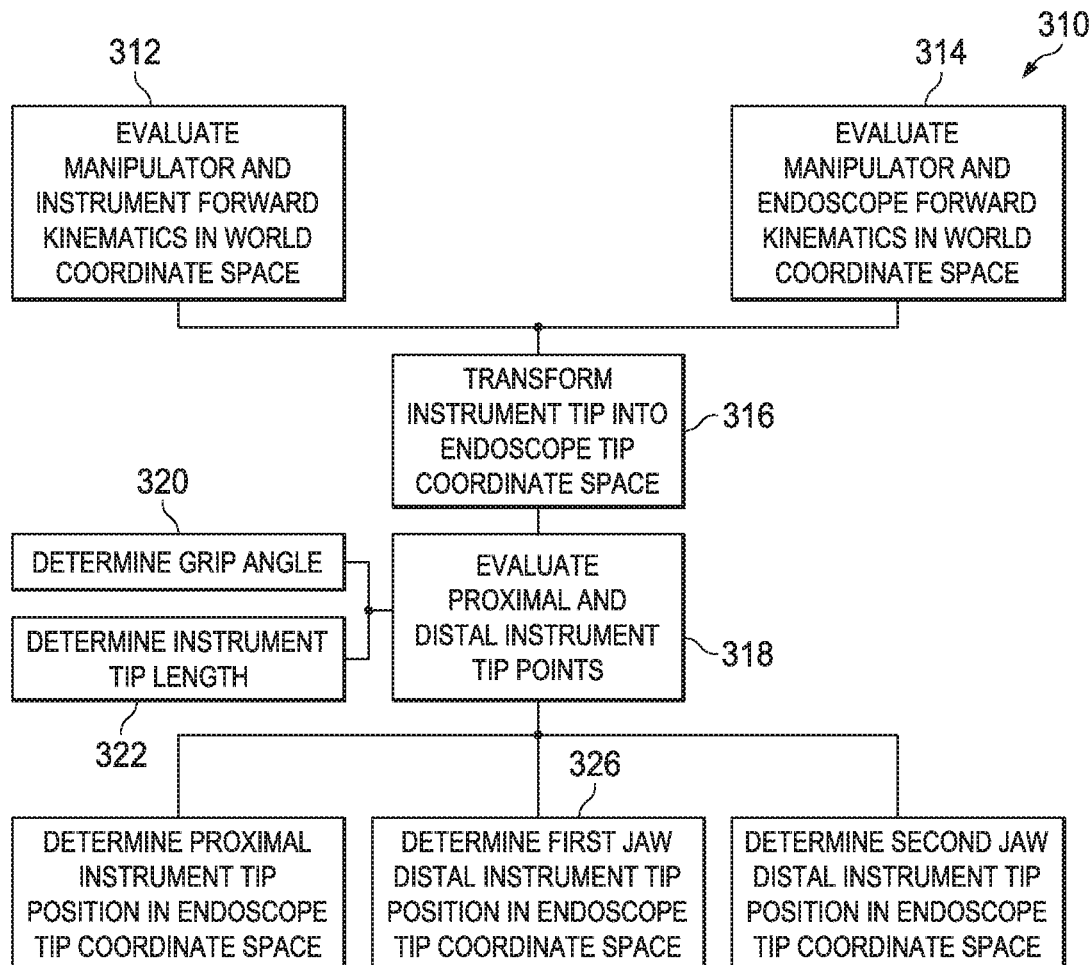
FIG. 7 is a method for evaluating instrument tip positions.

FIG. 7 illustrates a method 310 for evaluating instrument tip positions in the endoscope tip coordinate space. In the method 310, the forward kinematics of the teleoperational system and medical instruments is evaluated to determine the position of landmarks on the instrument tips, such as the proximal and distal tip portions, within the endoscope coordinate system. The evaluation uses forward kinematic and rigid body transformations. A process 312 includes evaluating the manipulator (e.g. manipulator 51) and instrument (e.g., instrument 206, 208) forward kinematic position data in the world coordinate space. A process 314 includes evaluating the manipulator and endoscope (e.g., imaging instrument 204) forward kinematic position data in the world coordinate space. A process 316 includes transforming the instrument tip position data into endoscope tip coordinate space. A process 320 includes determining a gripping angle (e.g., the angle between the distal tip portions 214, 216) for the distal tip portions. A process 322 includes determining a length of the instrument tip (e.g., a length between the proximal tip portion 212 and the distal tip portions 214, 216). At a process 318, the gripping angle and instrument tip length are used to evaluate the position of the proximal and distal instrument tip points. At a process 324, the proximal tip portion position is determined in endoscope tip coordinate space. At a process 326, a first distal tip portion (e.g., portion 214) position is determined in the endoscope tip coordinate space. At a process 328, a second distal tip portion (e.g., portion 216) position is determined in the endoscope tip coordinate space.

Figure 8:
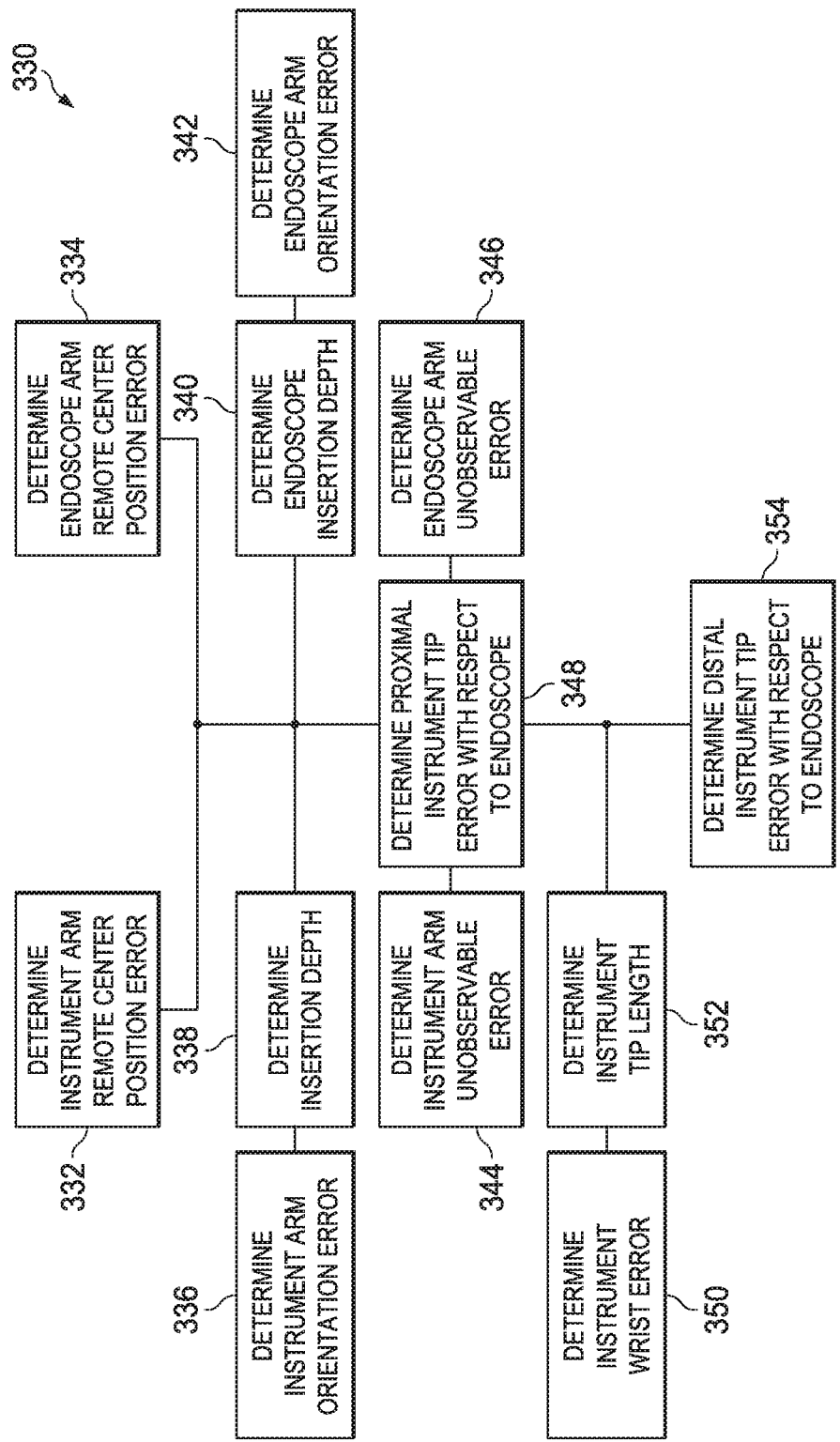
FIG. 8 is a method for estimating instrument tip position error in an imaging instrument coordinate space.

FIG. 8 illustrates a method 330 for estimating instrument tip position error with respect to the endoscope. Because of the large number of links in the kinematic chain of the teleoperational system and the variability of the manipulator poses, the instrument tip position error can be highly dependent upon configuration with variations ranging, for example, from 0.5 cm to 2.0 cm. An overall upper bound on error may be assumed for all configurations, but this overall approach would likely overestimate error as compared to an estimation for a particular configuration. In method 330 the tip position error is modeled as a summation of error contributed by the major constituent parts of the kinematic chain. For example, when the instruments are working close to the remote center (i.e., a small insertion depth) the majority of the tip position error may be contributed by the set-up joints while very little of the error is contributed by the manipulator.

The method 330 includes a process 332 for determining the instrument manipulator arm remote center position error and a process 334 for determining the endoscope manipulator arm remote center position error. The remote center position of a manipulator arm is determined by its setup joint sensors and fixed mechanical offsets between the links of the kinematic chain of the teleoperational assembly. An end-to-end kinematic calibration procedure may be performed to account for variability in manufacturing and assembly. The resultant position error may be due to non-linearity in the setup joint sensors, resolution of the sensors, and deflection of the assembly during calibration. The remote center position of a manipulator arm is independent of whether the arm has a medical instrument or imaging instrument installed. The manipulator arm remote center position error is relative between two arms, one of which has an instrument and the other of which has an imaging instrument.

The method 330 further includes a process 336 for determining an instrument manipulator arm orientation error and a process 342 for determining an instrument manipulator arm orientation error. The arm orientation error relates to the error in the pointing direction of the manipulator spar which is affected by the accuracy of the outer pitch and yaw joints of the manipulator and any misalignment in mounting of the manipulator to the setup structure of the teleoperational assembly. At process 338 the instrument arm orientation error is combined with the insertion depth. At 340, the endoscope arm orientation error is combined with the endoscope insertion depth. At process 344 an instrument arm unobservable error is determined, and at process 346 an endoscope arm unobservable error is determined. The unobservable errors account for errors that cannot be observed from the joint position sensors. The primary error is deflection of the setup joints due to loads incurred at the patient body wall. This directly affects the position of the remote center. Another error factor that may account for deflection of the instrument shaft is compliance, which may be a function of insertion depth. At process 348, all of the error factors determined in processes 332-346 are combined to determine the proximal portion tip error with respect to the endoscope. The method further includes a process 350 for determining instrument wrist error and a process 352 for determining instrument tip length. At process 354, the error factors from processes 350 and 352 are combined with the proximal portion tip error from process 348 to determine distal instrument tip error with respect to the endoscope.

Figure 9:
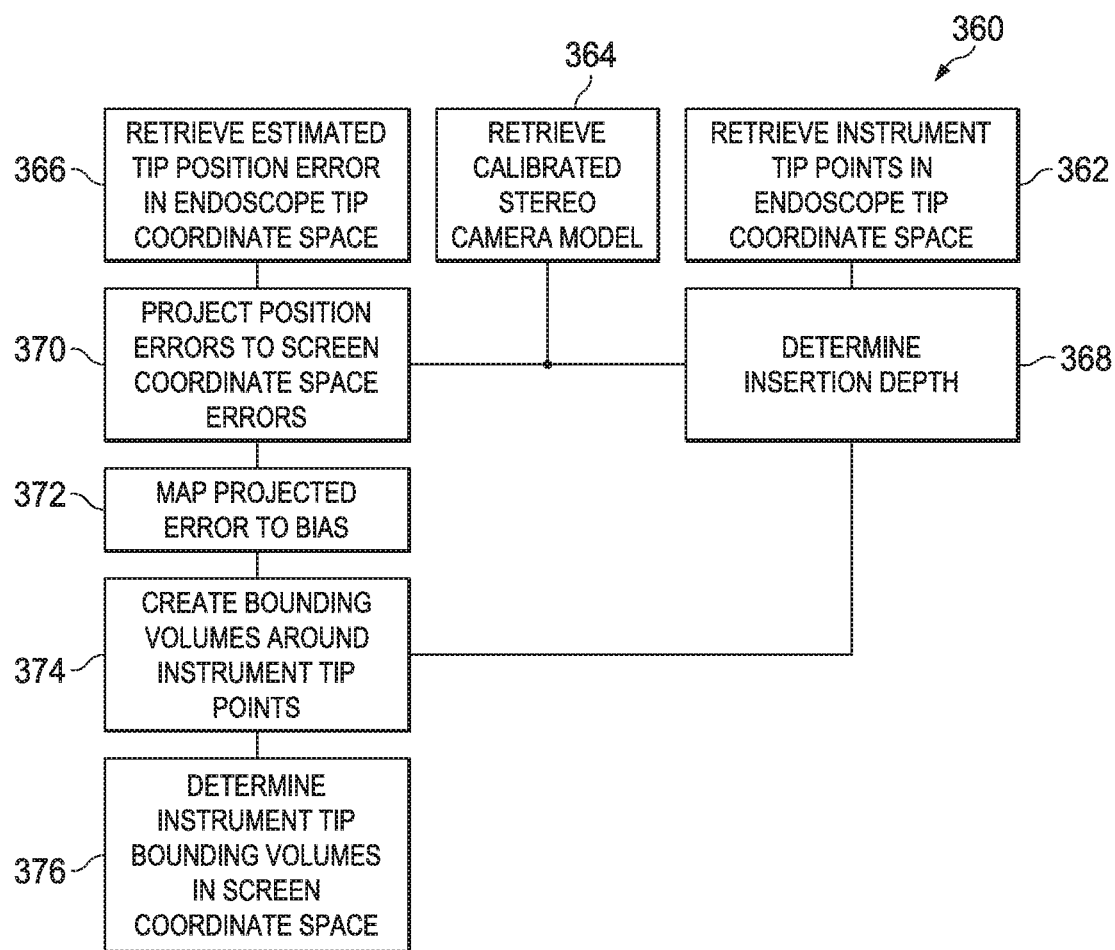
FIG. 9 is a method for determining an instrument tip bounding volume in a screen coordinate space.

FIG. 9 illustrates a method 360 for determining the instrument tip bounding volumes in the screen coordinate space. The method 360 combines the instrument tip positions from method 310 with the estimated position errors from method 330. In method 360, the position errors are mapped to the screen and the amount of the error to use as a bias for field of view testing is determined. The position error is the basis for determining bias for in/out of field of view testing. The position error can thus artificially grow or shrink the bounding volumes of the instrument tip portions to affect the balance of false positive and false negative errors when detecting whether an instrument tip is inside or outside of the imaging instruments field of view.

The method 360 includes a process 362 of retrieving the instrument tip portion positions in endoscope tip space, a process 364 of retrieving a calibrated stereo camera model, and a process 366 of retrieving estimated instrument tip position errors in endoscope tip coordinate space. At process 370, the tip position errors are projected to screen-space (e.g., from the stereo camera model) coordinate system position errors. At a process 372, the projected position errors are mapped a bias. When the bias is zero, the system will report a mix of false positive (i.e., incorrectly reporting out-of-view indicator) and false negative (i.e., out-of-view indicator not presented when it should have been presented) errors. When the bias is large (e.g., 100% bias), the system will only detect an instrument is out of the field of view when it is substantially outside of the field of view. The process of mapping the estimated position error to a bias allows the trade-off between no-bias and full-bias to be tuned. Minimize overt false positive errors is important because out-of-view indicators can be distracting and confusing if presented when the instrument tip is clearly visible in the field of view. Too many false positive errors can desensitize the clinician to the alerts such that the clinician comes to ignore subsequent true positive detections. When the instrument tip get close to the endoscope tip (i.e., the instrument tip takes up a large portion of the field of view), the size of the tip position error approaches the cross-sectional dimensions of the field of view volume. In this configuration, without the use of a bias, there would be a high rate of false positive detections. FIGS. 11-15 illustrate in greater detail the use of bias.

At process 368, the insertion depth of the instrument tip is determined. At process 374, bounding volumes (e.g., 290, 292, 294, 296, 522, 524) are created around instrument tip points. At process 376, the instrument tip bounding volumes are determined in the screen space coordinate system. Ordinarily the bounding volumes are not displayed to a user, but optionally they may be.

Figure 10:
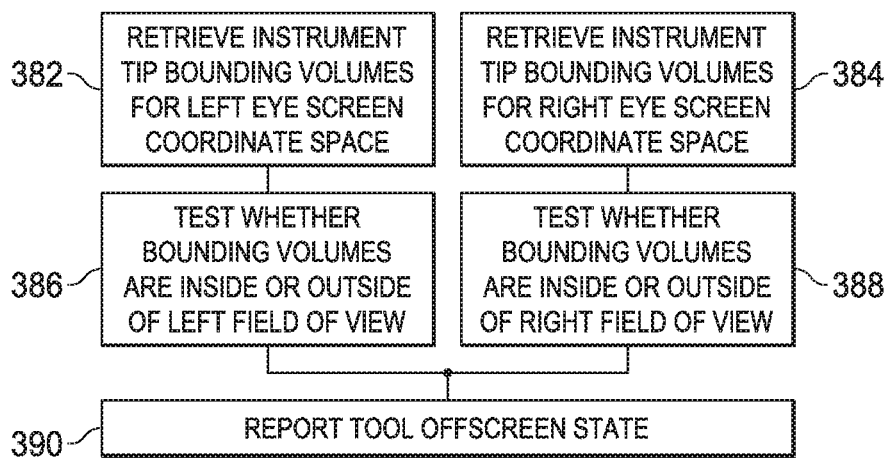
FIG. 10 is a method for determining if an instrument tip is outside of an imaging instrument field of view.

FIG. 10 is a method for determining if an instrument tip is outside of an imaging instrument field of view. At a process 382, the instrument tip bounding volumes are retrieved for the left eye screen coordinate space, and at process 384, the instrument tip bounding volumes are retrieved for the right eye screen coordinate space. At a process 386, a test is conducted to determine whether the bounding volumes are inside or outside of the left field of view. At a process 388, a test is conducted to determine whether the bounding volumes are inside or outside of the right eye field of view. At a process 390 an out-of-view indicator is presented to the clinician if all of the bounding volumes are outside of the fields of view.

Figure 11:
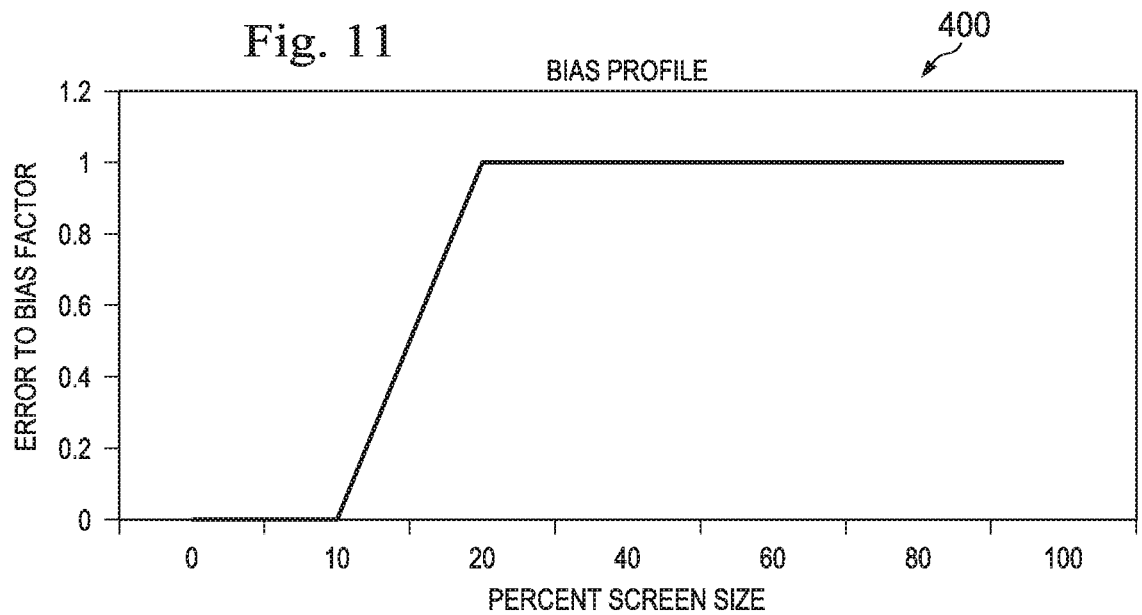
FIG. 11 is a bias profile used in the method of FIG. 6.

FIG. 11 illustrates a bias profile 400 for mapping the projected position error to a bias factor to determine how much of the position error to use for biasing the tool out-of-view indicators. The bias profile 400 applies full bias (bias factor=1) when the apparent size of the position error is large (e.g., when the position error size is 20% or greater of the screen size). This generally occurs when the instrument tip is very close to the endoscope tip. The bias profile reduces the bias (e.g., bias factor<1) when the apparent size of the error is small (e.g., when the position error size is less than 20% of the screen size). This generally occurs when the instrument tip is far from the endoscope. This mapping method provides a direct way to tune out-of-view detection process based upon perceived error and may be independent of assumptions about instrument depth.

Figure 12:
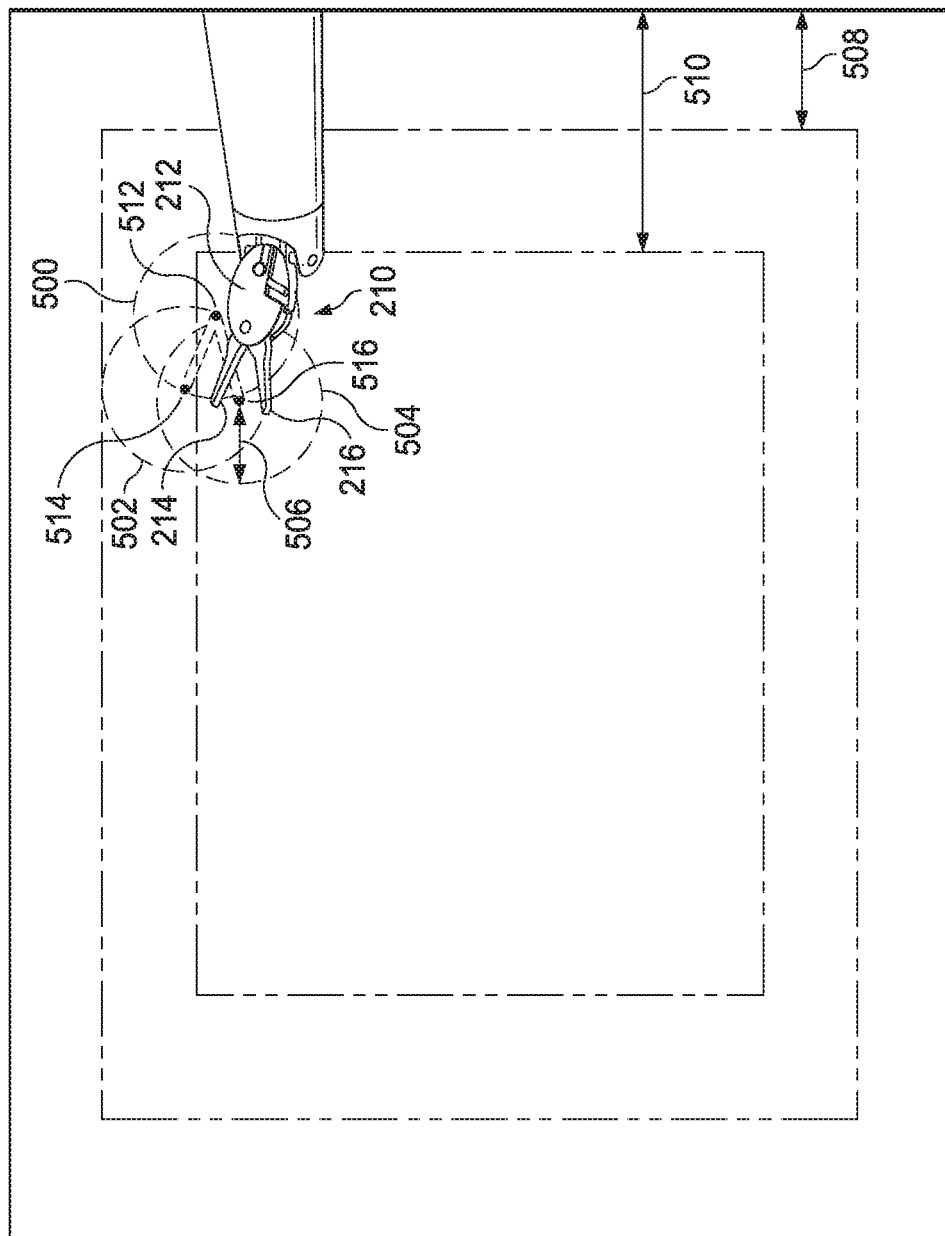

FIG. 12-15 illustrates the use of the bias profile 400. FIG. 12 illustrates position error 500 for the proximal tip portion 212 of the instrument tip 210. A position error 502 is shown for the distal tip portion 214 and a position error 504 is shown for the distal tip portion 216. The position error circles 500, 502, 504 represent the estimate of the upper bound of the instrument position error for the tip portion. An error radius 506 is also identified. A dimension 508 is 10% of the screen size, and a dimension 510 is 20% of the screen size. Points 512, 514, 516 correspond to points 212, 214, and 216, respectively and represent an overlay of the system's absolute sense of the instrument tip position relative to the endoscope tip. In this configuration with the instrument tip relatively far from the endoscope tip, the error radius 506 is smaller than 10% of the screen size. Based upon the bias profile 400, no bias is applied to the tip positions 512-516 and instead the positions 512-516 are used. The connecting segments themselves are used as the bounding volumes to determine whether the instrument tip is inside or outside of the field of view.

Figure 13:
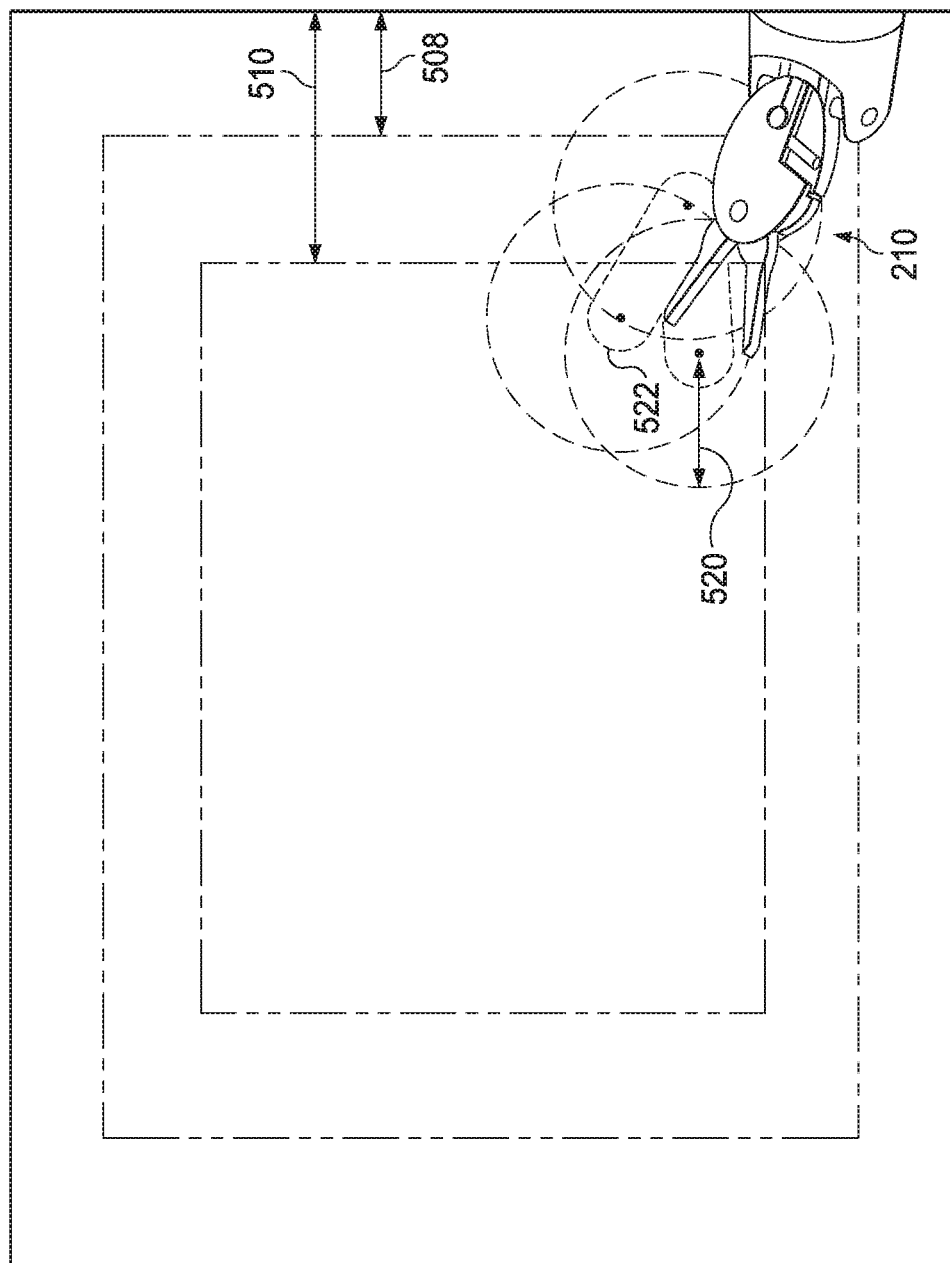

FIG. 13 illustrates the instrument tip 210 at a medium distance from the endoscope tip. In this configuration the error radius 520 of the position error is between the 10% dimension 508 and the 20% dimension 510. Based upon the bias profile 400, a bounding volume 522 is determined as a percentage (between 0% and 100%) of the full position errors. This bounding volume 522 is used to determine whether the instrument tip is inside or outside of the field of view.

Figure 14:
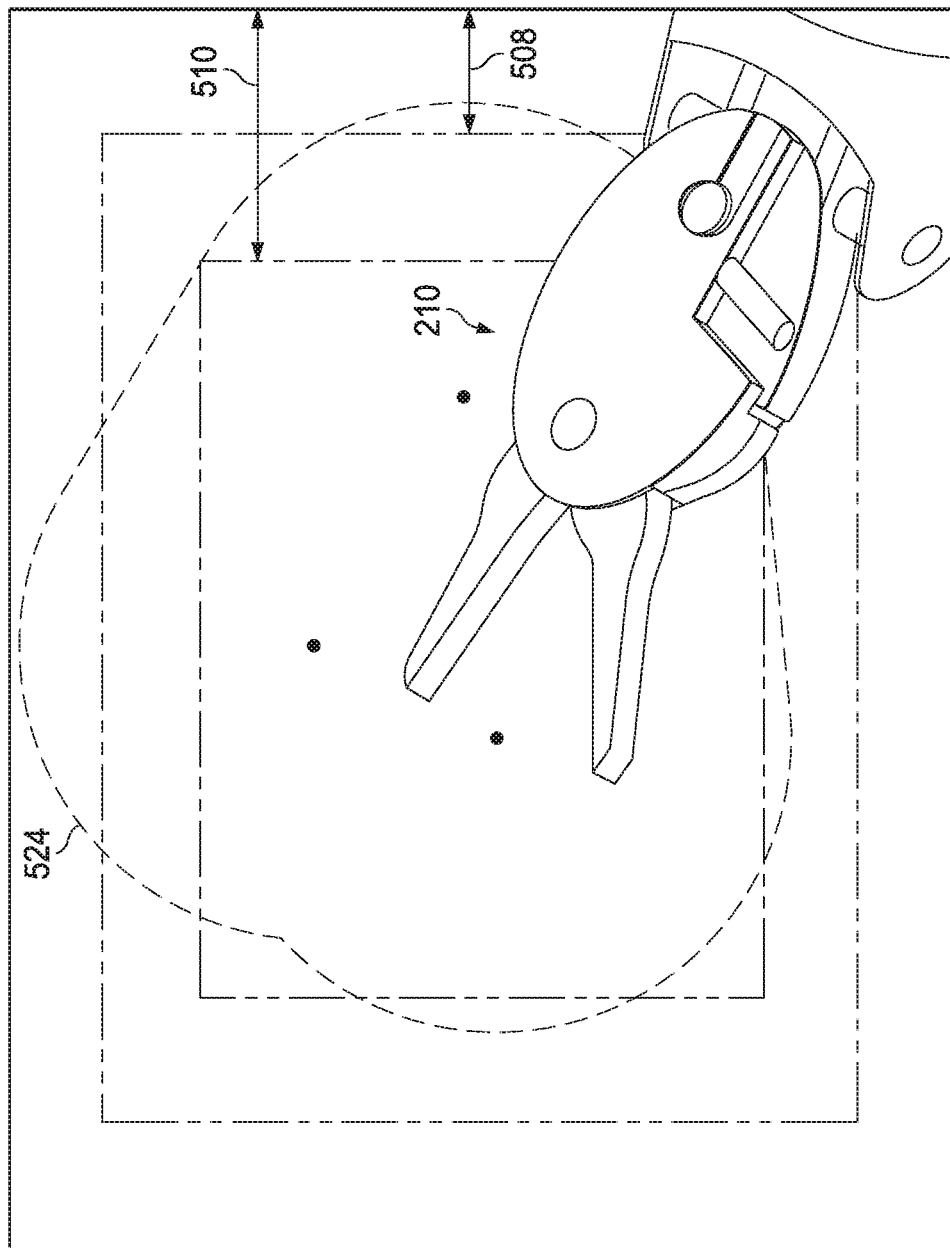

FIG. 14 illustrates the instrument tip 210 at a near distance from the endoscope tip. In this configuration the error radius is greater than the 20% dimension 510. Based upon the bias profile 400, a bounding volume 524 is determined to be the full position error. This bounding volume 524 is used to determine whether the instrument tip is inside or outside of the field of view. As shown in FIG. 15, if the points 512, 514, 516 were used to determine whether the instrument tip was inside or outside of the field of view, the system would falsely report an out-of-view indicator because points 512, 514, 516 are outside of the field of view. When the bounding volume 524 is used to test inside/outside field of view, the system determines that the bounding volume 524 is inside the field of view and thus does not report an out-of-view indicator.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical imaging system comprising:
   a teleoperational assembly configured to control movement of a medical instrument including an instrument tip; and
   a control system comprising a processing unit, the processing unit including one or more processors, wherein the processing unit is configured to:
      determine a position error for the instrument tip, wherein the position error is based on at least one error factor of the teleoperational assembly;
      determine a set of predicted positions for the instrument tip from the position error;
      determine at least one instrument tip bounding volume from the set of predicted positions for the instrument tip, wherein the at least one instrument tip bounding volume includes:
         a first volume, the first volume based on an error radius of a position error for a distal end of the instrument tip; and
         a second volume, the second volume based on an error radius of a position error for a proximal end of the instrument tip,
         wherein the first volume surrounds and moves with the distal end of the instrument tip, and wherein the second volume surrounds and moves with the proximal end of the instrument tip;
      determine whether the at least one instrument tip bounding volume is outside a field of view of an imaging instrument; and
      based on a determination that the at least one instrument tip bounding volume is outside the field of view, indicate the instrument tip is outside the field of view.

2. The system of claim 1 wherein indicating the instrument tip is outside the field of view includes generating an out-of-view instrument indicator for display with an image of the field of view.

3. The system of claim 2 wherein the out-of-view instrument indicator includes a graphical bar extending along at least one edge of the image of the field of view.

4. The system of claim 2 wherein the out-of-view instrument indicator includes a textual display related to the medical instrument.

5. The system of claim 1 wherein indicating the instrument tip is outside the field of view includes generating an audible out-of-view instrument indication.

6. The system of claim 1 wherein the field of view of the imaging instrument is a stereo field of view of a stereo imaging instrument.

7. The system of claim 1 wherein, based on the determination that the at least one instrument tip bounding volume is outside the field of view, the processing unit is further configured to:
   recognize a first context when the out-of-view instrument indicator is to be displayed; and
   recognize a second context when the out-of-view instrument indicator is not to be displayed.

8. The system of claim 1 wherein the position error for the instrument tip is determined from kinematic variability in the teleoperational assembly.

9. The system of claim 1 wherein the position error for the instrument tip is determined from kinematic variability in the medical instrument.

10. The system of claim 1 wherein the at least one instrument tip bounding volume is further based upon a distance of the instrument tip from a distal end of the imaging instrument.

11. The system of claim 1 wherein the processing unit is further configured to:
    generate a warning indicator if the instrument tip is within the field of view of the imaging instrument and within a predefined proximity to an edge of the field of view.

12. The system of claim 11 wherein the warning indicator includes a visual indicator for display with an image of the field of view.

13. The system of claim 1 further comprising the medical instrument.

14. A method of imaging, the method comprising:
    determining a position error for an instrument tip of a medical instrument controlled by a teleoperational assembly, wherein the position error is based on at least one error factor of the teleoperational assembly;
    determining a set of predicted positions for the instrument tip from the position error;
    determining at least one instrument tip bounding volume from the set of predicted positions for the instrument tip, wherein the at least one instrument tip bounding volume includes a first volume based on an error radius of a position error for a distal end of the instrument tip and a second volume based on an error radius of a position error for a proximal end of the instrument tip, wherein the first volume surrounds and moves with the distal end of the instrument tip, and wherein the second volume surrounds and moves with the proximal end of the instrument tom;
    determining whether the at least one instrument tip bounding volume is outside a field of view of an imaging instrument; and
    based on a determination that the at least one instrument tip bounding volume is outside the field of view, indicating the instrument tip is outside the field of view.

15. The method of claim 14 wherein indicating the instrument tip is outside the field of view includes generating an out-of-view instrument indicator for display with an image of the field of view.

16. The method of claim 15 wherein the out-of-view instrument indicator includes a graphical bar extending along at least one edge of the image of the field of view.

17. The method of claim 15 wherein the out-of-view instrument indicator includes textual information about the medical instrument.

18. The method of claim 14 wherein indicating the instrument tip is outside the field of view includes generating an audible out-of-view instrument indication.

19. The method of claim 14 wherein the field of view of the imaging instrument is a stereo field of view of a stereo imaging instrument.

20. The method of claim 14 wherein determining the position error for the instrument tip includes determining the position error from kinematic variability in the teleoperational assembly.

21. The method of claim 14 wherein determining the position error for the instrument tip includes determining the position error from kinematic variability in the medical instrument.

22. The method of claim 14 wherein determining the at least one instrument tip bounding volume includes determining a bounding volume based upon a distance of the instrument tip from a distal end of the imaging instrument.

23. The method of claim 14 wherein determining the at least one instrument tip bounding volume includes determining a bounding volume based upon a projected size of the position error on a display.

24. The method of claim 14 further comprising:
generating a warning indicator if the instrument tip is within the field of view of the imaging instrument and within a predefined proximity to an edge of the field of view.

25. The method of claim 24 wherein the warning indicator includes a visual indicator for display with an image of the field of view.

26. The method of claim 14 further comprising:
receiving an acknowledgement of an out-of-view instrument status for the medical instrument; and
responsive to the received out-of-view instrument status, enabling functionality of the medical instrument.

27. The system of claim 1 wherein the processing unit is further configured to:
receive an acknowledgement of an out-of-view instrument status for the medical instrument; and
responsive to the received out-of-view instrument status, enable functionality of the medical instrument.

28. The system of claim 1 wherein the set of predicted positions for the instrument tip includes predicted positions for the instrument tip to a degree of certainty of at least 90%.

29. The system of claim 1 wherein determining whether the at least one instrument tip bounding volume is outside the field of view of the imaging instrument comprises determining that both the first volume and the second volume are outside the field of view.

30. The method of claim 14 wherein determining whether the at least one instrument tip bounding volume is outside the field of view of the imaging instrument comprises determining that both the first volume and the second volume are outside the field of view.

* * * * *

UNITED STATES PATENT AND TRADEMARK OFFICE
CERTIFICATE OF CORRECTION

| | |
|---|---|
| PATENT NO. | : 11,317,979 B2 |
| APPLICATION NO. | : 15/262867 |
| DATED | : May 3, 2022 |
| INVENTOR(S) | : Brandon D. Itkowitz, Brian D. Hoffman and Paul W. Mohr |

It is certified that error appears in the above-identified patent and that said Letters Patent is hereby corrected as shown below:

In the Specification

Column 1, Please replace first paragraph as follows:
--This patent application is the U.S. national phase of International Application No. PCT/US2015/021109, filed Mar. 17, 2015, which designated the U.S. and claims priority to and the benefit of the filing date of U.S. Provisional Patent Application 61/954,442, titled "Systems and Methods for Offscreen Indication of Instruments in a Teleoperational Medical System," filed Mar. 17, 2014, which are incorporated herein by reference in their entirety.--

In the Claims

Column 16, Claim 14, Line 33, please replace the word "tom" with --tip--

Signed and Sealed this
Fifth Day of July, 2022

Katherine Kelly Vidal
*Director of the United States Patent and Trademark Office*